US007641907B2

(12) United States Patent
Kinney et al.

(10) Patent No.: US 7,641,907 B2

(45) Date of Patent: Jan. 5, 2010

(54) DENGUE SEROTYPE 1 ATTENUATED STRAIN

(75) Inventors: Richard Kinney, Fort Collins, CO (US); Claire Y. H. Kinney, Fort Collins, CO (US); Véronique Barban, Craponne (FR); Jean Lang, Mions (FR); Bruno Guy, Lyons (FR)

(73) Assignees: Sanofi Pasteur, Lyons (FR); Center for Disease Control and Prevention, Atlanta, GA (US)

(*) Notice: Subject to any disclaimer, the term of this patent is extended or adjusted under 35 U.S.C. 154(b) by 121 days.

(21) Appl. No.: 11/449,876

(22) Filed: Jun. 9, 2006

(65) Prior Publication Data

US 2006/0292172 A1 Dec. 28, 2006

Related U.S. Application Data

(60) Provisional application No. 60/691,243, filed on Jun. 17, 2005.

(51) Int. Cl.
*A61K 39/12* (2006.01)

(52) U.S. Cl. ................................ 424/218.1; 424/186.1

(58) Field of Classification Search ...................... None
See application file for complete search history.

(56) References Cited

U.S. PATENT DOCUMENTS

2004/0137013 A1 7/2004 Katinger et al.

FOREIGN PATENT DOCUMENTS

| | | |
|---|---|---|
| EP | 1 159 968 | 12/2001 |
| WO | WO-96/40933 | 12/1996 |
| WO | WO-00/57907 | 10/2000 |
| WO | WO-02/095075 | 11/2002 |
| WO | WO-03/092592 | 11/2003 |

OTHER PUBLICATIONS

Gowen et al., Antiviral Research, 2008, 78:79-90.*

Sanchez et al. Vaccine, 2006, 24:4914-4926.*

Database EMBL [Online] Sep. 18, 2002, "Dengue virus type 1 recombinant clone rDEN1, complete genome." XP002397884 retrieved from EBI accession No. EM_PRO:AY145121, Database accession No. AY145121 nt 5962 ->A.

Kinney et al, "Development of new vaccine against dengue fever and Japanese encephalitis", 2001, pp. 176-197, vol. 44, Intervirology.

Kinney et al, "Construction of Infectious cDNA for Dengue 2 Virus: Strain 16681 and its attenuated Vaccine Derivative, Strain PDK-53", Apr. 14, 1997, pp. 300-308, vol. 230, No. 2, Academic Press Orlando, Florida, USA.

Butrapet et al, "Attenuation markers of a candidate dengue type 2 vaccine virus, strain 16681 (PDK-53), are defined by mutations in the 5' noncoding region and nonstructural proteins 1 and 3", Apr. 2000, pp. 3011-3019, vol. 74, No. 7, Journal of Virology, The American Society for Microbiology, USA.

Putnak et al, "Development of a purified, inactivated, dengue-2 virus vaccine prototype in vero cells: Immunogenicity and protection in mice and rhesus monkeys", Dec. 1996, pp. 1176-1184, vol. 174, No. 6, Journal of Infectious Diseases, Chicago, IL, USA.

Montagnon et al, "Experience with vero cells at Pasteur merieux connaught developments in biological standardization", 1997, pp. 137-140, vol. 98, Developments in Biological Standardization, Karger, Basel, CH.

* cited by examiner

*Primary Examiner*—Stacy B Chen
(74) *Attorney, Agent, or Firm*—B. Aaron Schulman; Terry L. Wright; Stites & Harbison PLLC

(57) ABSTRACT

The invention relates to live attenuated VDV1 (VERO-Derived Dengue serotype 1 virus) strains which have been derived from the wild-type dengue-1 strain 16007 by passaging on PDK and sanitization on Vero cells. The invention further relates to a vaccine composition which comprises a VDV1 strain.

10 Claims, 5 Drawing Sheets

SEQUENCE LISTING

```
<160> NUMBER OF SEQ ID NOS: 44

<210> SEQ ID NO 1
<211> LENGTH: 10735
<212> TYPE: DNA
<213> ORGANISM: Dengue virus
<220> FEATURE:
<221> NAME/KEY: misc_feature
<222> LOCATION: (1)..(10654)
<223> OTHER INFORMATION: VDV1

<400> SEQUENCE: 1

agttgttagt ctacgtggac cgacaagaac agtttcgaat cggaagcttg cttaacgtag     60

ttctaacagt tttttattag agagcagatc tctgatgatc aaccaacgaa aaaagacggg    120

tcgaccgtct ttcaatatgc tgaaacgcgc gagaaaccgc gtgtcaactg tttcacagtt    180

ggcgaagaga ttctcaaaag gattgctctc aggccaagga cccatgaaat tggtgatggc    240

tttcatagca ttcttaagat ttctagccat acccccaaca gcaggaattt tggctagatg    300

gggctcattc aagaagaatg gagcgattaa agtgttacgg ggtttcaaga gagaaatctc    360

aaacatgcta aacataatga acaggaggaa aagatccgtg accatgctcc ttatgctgct    420

gcccacagcc ctggcgttcc atctgacgac acgaggggga gagccgcata tgatagttag    480

caagcaggaa agaggaaagt cacttttgtt caagacctct gcaggtgtca acatgtgcac    540

cctcattgcg atggatttgg gagagttgtg tgaggacacg atgacctaca aatgcccccg    600

gatcactgag gcggaaccag atgacgttga ctgttggtgc aatgccacgg acacatgggt    660

gacctatgga acgtgctctc aaactggcga acaccgacga gacaaacgtt ccgtcgcatt    720

ggccccacac gtggggcttg gcctagaaac aagagccgaa acgtggatgt cctctgaagg    780

tgcttggaaa cagatacaaa aagtagagac ttgggctctg agacatccag gattcacggt    840

gatagccctt tttctagcac atgccatagg aacatccatc acccagaaag ggatcatttt    900

cattttgctg atgctggtaa caccatctat ggccatgcga tgcgtgggaa taggcaacag    960

agacttcgtg gaaggactgt caggagcaac atgggtggat gtggtactgg agcatggaag   1020

ttgcgtcacc accatggcaa aaaacaaacc aacactggac attgaactct tgaagacgga   1080

ggtcacaaac cctgcagttc tgcgtaaatt gtgcattgaa gctaaaatat caaacaccac   1140

caccgattcg agatgtccaa cacaaggaga agccacactg gtggaagaac aagacgcgaa   1200

ctttgtgtgc cgacgaacgt tcgtggacag aggctggggc aatggctgtg ggctattcgg   1260

aaaaggtagt ctaataacgt gtgccaagtt taagtgtgtg acaaaactag aaggaaagat   1320

agctcaatat gaaaacctaa aatattcagt gatagtcacc gtccacactg gagatcagca   1380

ccaggtggga aatgagacta cagaacatgg aacaactgca accataacac ctcaagctcc   1440

tacgtcggaa atacagctga ccgactacgg aacccttaca ttagattgtt cacctaggac   1500

agggctagat tttaacgaga tggtgttgct gacaatgaaa aagaaatcat ggcttgtcca   1560
```

-continued caaacagtgg tttctagact taccactgcc ttggacctct ggggctttaa catcccaaga 1620
gacttggaac agacaagatt tactggtcac atttaagaca gctcatgcaa agaagcagga 1680
agtagtcgta ctaggatcac aagaaggagc aatgcacact gcgctgactg gagcgacaga 1740
aatccaaacg tcaggaacga caacaatttt cgcaggacac ctaaaatgca gactaaaaat 1800
ggacaaacta actttaaaag ggatgtcata tgtgatgtgc acaggctcat tcaagttaga 1860
gaaagaagtg gctgagaccc agcatggaac tgttctggtg caggttaaat atgaaggaac 1920
agacgcacca tgcaagattc ccttttcgac ccaagatgag aaaggagcaa cccagaatgg 1980
gagattaata acagccaacc ccatagtcac tgacaaagaa aaaccagtca atattgaggc 2040
agaaccaccc tttggtgaga gctacatcgt ggtaggagca ggtgaaaaag ctttgaaact 2100
aagctggttc aagaaaggaa gcagcatagg gaaaatgttt gaagcaactg cccgaggagc 2160
acgaaggatg gccattctgg gagacaccgc atgggacttc ggttctatag gaggagtgtt 2220
cacgtctatg ggaaaactgg tacaccaggt ttttggaact gcatatggag ttttgtttag 2280
cggagtttct tggaccatga aaataggaat agggattctg ctgacatggc taggattaaa 2340
ttcaaggaac acgtcccttt cggtgatgtg catcgcagtt ggcatggtca cactgtacct 2400
aggagtcatg gttcaggcag attcgggatg tgtaatcaac tggaaaggca gagaacttaa 2460
atgtggaagc ggcatttttg tcactaatga agttcacact tggacagagc aatacaaatt 2520
ccaggctgac tcccccaaga gactatcagc agccattggg aaggcatggg aggagggtgt 2580
gtgtggaatc cgatcagcca ctcgtctcga gaacatcatg tggaaacaaa tatcaaatga 2640
attgaaccac atcctacttg aaaatgacat gaaatttaca gtggtcgtgg gagacgttag 2700
tggaatcttg gcccaaggaa aaaaaatgat taggccacaa cccatggaac acaaatactc 2760
gtggaaaagc tggggaaaag ctaaaatcat aggagcggat gtacagaaca ccaccttcat 2820
catcgacggc ccaaacaccc cagaatgccc tgacaatcaa agagcatgga atatttggga 2880
agtagaggac tatggatttg ggattttcac gacaaacata tggttgaaat tgcgtgactc 2940
ctacacccaa gtatgtgacc accggctgat gtcagctgcc attaaggaca gcaaggcagt 3000
ccatgctgac atggggtact ggatagaaag tgaaaagaac gagacatgga agttggcgag 3060
agcctccttt atagaagtta agacatgcat ctggccaaaa tcccacactc tatggagcaa 3120
tggagttctg gaaagtgaaa tgataattcc aaagatatat ggaggaccaa tatctcagca 3180
caactacaga ccaggatatt tcacacaaac agcagggccg tggcacctag gcaagttgga 3240
actagatttc gatttttgtg aaggtaccac agttgttgtg gatgaacatt gtggaaatcg 3300
aggaccatct ctcagaacca caacagtcac aggaaagata atccatgaat ggtgctgcag 3360
atcttgtacg ctacccccc tacgtttcaa aggggaagac gggtgttggt acggcatgga 3420
aatcagacca gtgaaggaca aggaagagaa cctggtcaag tcaatggtct ctgcagggtc 3480
aggagaagtg gacagctttt cactaggact gctatgcata tcaataatga ttgaagaagt 3540
gatgagatcc agatggagca aaaaaatgct gatgactgga acactggctg tgttcctcct 3600
tcttataatg ggacaattga catggagtga tctgatcagg ttatgtatta tggttggagc 3660
caacgcttca gacaagatgg ggatgggaac aacgtaccta gctttaatgg ccactttcaa 3720
aatgagacca atgttcgccg tcgggctatt atttcgcaga ctaacatcta gagaagttct 3780
tcttcttaca attggcttga gcctggtggc atccgtggag ctaccaagtt ccctagagga 3840
gctgggggat ggacttgcaa taggcatcat gatgttgaaa ttattgactg attttcagtc 3900
acaccagcta tgggctactc tgctatcctt gacatttatt aaaacaactt tttcattgca 3960

-continued

```
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag accccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa aaaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
```

-continued tcgctggttg gacgccagaa catactctga cccactggct ctgcgcgagt ttaaagagtt 6360
tgcagcagga agaagaagcg tctcaggtga cctaatatta gaaataggga aacttccaca 6420
acatttgacg caaagggccc agaatgcttt ggacaacttg gtcatgttgc acaattccga 6480
acaaggagga aaagcctata gacatgctat ggaagaactg ccagacacaa tagaaacgtt 6540
gatgctccta gccttgatag ctgtgttgac tggtggagtg acgctgttct tcctatcagg 6600
aagaggtcta ggaaaaacat ctatcggctt actctgcgtg atggcctcaa gcgcactgtt 6660
atggatggcc agtgtggagc cccattggat agcggcctcc atcatactgg agttctttct 6720
gatggtactg cttattccag agccagacag acagcgcact ccacaggaca accagctagc 6780
atatgtggtg ataggtctgt tattcgtgat attgacagtg gcagccaatg agatgggatt 6840
attggaaacc acaaagaaag acctggggat tggccatgta gctgctgaaa accaccacca 6900
tgctacaatg ctggacgtag acctacatcc agcttcagcc tggaccctct atgcagtggc 6960
cacaacaatc atcactccta tgatgagaca cacaattgaa aacacaacgg caaatatttc 7020
cctgacagcc atcgcaaacc aagcagctat attgatggga cttgacaagg gatggccaat 7080
atcgaagatg gacataggag ttccacttct cgccttgggg tgctattccc aagtgaatcc 7140
gctgacactg atagcggcag tattgatgct agtagctcat tacgccataa ttggacctgg 7200
actgcaagca aaagctacta gagaagctca aaaaagaaca gcggctggaa taatgaaaaa 7260
tccaactgtc gacgggattg ttgcaataga cttagatccc gtggtttacg atgcaaaatt 7320
tgaaaaacag ctaggccaaa taatgttgtt gatactttgc acatcacaga ttcttttgat 7380
gcggactaca tgggccttgt gtgaatccat cacattggct actggacctc tgaccactct 7440
ttgggaggga tctccaggaa aattctggaa caccacaata gcggtatcca tggcaaacat 7500
tttcaggggg agttatctag caggagcagg tctggccttc tcattaatga aatctctagg 7560
aggaggtagg agaggcacgg gagcccaagg ggaaacactg ggagaaaaat ggaaaagaca 7620
actaaaccaa ctgagcaagt cagaattcaa tacttacaag aggagtggga ttatggaggt 7680
ggatagatcc gaagccaaag agggactgaa aagaggagaa acaaccaaac acgcagtatc 7740
gagaggaacg gccaaactga ggtggttcgt ggagaggaac cttgtgaaac cagaagggaa 7800
agtcatagac ctcggttgtg gaagaggtgg ctggtcatat tattgcgctg ggctgaagaa 7860
agtcacagaa gtgaaaggat acacaaaagg aggacctgga catgaggaac caatcccaat 7920
ggcgacctat ggatggaacc tagtaaggct gcactccgga aaagatgtat tttttatacc 7980
acctgagaaa tgtgacaccc ttttgtgtga tattggtgag tcctctccga acccaactat 8040
agaggaagga agaacgttac gtgttctgaa aatggtggaa ccatggctca gaggaaacca 8100
attttgcata aaaattctaa atccctatat gccgagcgtg gtagaaactc tggaacaaat 8160
gcaaagaaaa catggaggaa tgctagtgcg aaacccactc tcaagaaatt ccacccatga 8220
aatgtactgg gtttcatgtg gaacaggaaa cattgtgtca gcagtaaaca tgacatctag 8280
aatgttgcta aatcggttca caatggctca caggaagcca acatatgaaa gagacgtgga 8340
cttaggcgct ggaacaagac atgtggcagt agaaccagag gtagccaacc tagatatcat 8400
tggccagagg atagagaata taaaaaatga acataagtca acatggcatt atgatgagga 8460
caatccatac aaaacatggg cctatcatgg atcatatgag gttaagccat caggatcggc 8520
ctcatccatg gtcaatggcg tggtgagatt gctcaccaaa ccatgggatg ttatccccat 8580
ggtcacacaa atagccatga ctgataccac acccctttgga caacagaggg tgtttaaaga 8640
gaaagttgac acgcgcacac caaaagcaaa acgtggcaca gcacaaatta tggaagtgac 8700

-continued

```
agccaggtgg ttatggggtt tcctttctag aaacaaaaaa cccagaattt gcacaagaga   8760

ggagtttaca agaaaagtta ggtcaaacgc agctattgga gcagtgttcg ttgatgaaaa   8820

tcaatggaac tcggcaaaag aagcagtgga agacgaacgg ttctgggaac ttgtccacag   8880

agagagggag cttcataaac aggggaaatg tgccacgtgt gtctacaata tgatggggaa   8940

gagagagaaa aaattaggag agttcggaaa ggcaaaagga agtcgtgcaa tatggtacat   9000

gtggttggga gcacgcttcc tagagtttga agcccttggt ttcatgaatg aagatcactg   9060

gttcagtaga gagaattcac tcagtggagt ggaaggagaa ggactccaca aacttggata   9120

catactcaga gacatatcaa ggattccagg ggggaacatg tatgcagatg acacagccgg   9180

atgggacaca agaataacag aggatgatct ccagaatgag gctaaaatca ctgacatcat   9240

ggagcccgaa catgccctgc tggctacgtc aatctttaag ctgacctacc aaaataaggt   9300

ggtaagggtg cagagaccag caaaaaatgg aaccgtgatg gatgttatat ccagacgtga   9360

ccagagaggc agtggacagg ttggaactta tggcttaaac actttcacca acatggaggc   9420

ccaactgata agacaaatgg agtctgaggg aatcttttta cccagcgaat tggaaacccc   9480

aaatctagcc ggaagagttc tcgactggtt ggaaaaatat ggtgtcgaaa ggctgaaaag   9540

aatggcaatc agcggagatg actgtgtggt gaaaccaatt gatgacaggt tcgcaacagc   9600

cttaacagct ttgaatgaca tgggaaaagt aagaaaagac ataccacaat gggaaccttc   9660

aaaaggatgg aatgattggc aacaagtgcc tttctgttca caccacttcc accagctaat   9720

tatgaaggat gggagggaga tagtggtgcc atgccgcaac caagatgaac ttgtggggag   9780

ggccagagta tcacaaggcg ccggatggag cctgagagaa accgcatgcc taggcaagtc   9840

atatgcacaa atgtggcagc tgatgtattt ccacaggaga gacctgagac tggcggctaa   9900

cgctatttgt tcagccgttc cagttgattg ggtcccaacc agccgcacca cctggtcgat   9960

ccatgcccat caccaatgga tgacaacaga agacatgtta tcagtatgga atagggtctg  10020

gatagaggaa aacccatgga tggaggataa gactcatgtg tccagttggg aagaagttcc  10080

atacctagga aagagggaag atcagtggtg tggatccctg ataggcttaa cagcaagggc  10140

cacctgggcc actaatatac aagtggccat aaaccaagtg agaaggctca ttgggaatga  10200

gaattatcta gattacatga catcaatgaa gagattcaag aatgagagtg atcccgaagg  10260

ggcactctgg taagtcaaca cattcacaaa ataaaggaaa ataaaaaatc aaatgaggca  10320

agaagtcagg ccagattaag ccatagtacg gtaagagcta tgctgcctgt gagccccgtc  10380

caaggacgta aaatgaagtc aggccgaaag ccacggtttg agcaagccgt gctgcctgtg  10440

gctccatcgt ggggatgtaa aaacccggga ggctgcaacc catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcgt  10620

aacaataaac agcatattga cgctgggaga gaccagagat cctgctgtct ctacagcatc  10680

attccaggca cagaacgcca gaaaatggaa tggtgctgtt gaatcaacag gttct       10735
```

```
<210> SEQ ID NO 2
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: Dengue virus type 1 strain 16007  polyprotein
      precursor, complete cds
```

-continued

<400> SEQUENCE: 2

```
agttgttagt ctacgtggac cgacaagaac agtttcgaat cggaagcttg cttaacgtag     60
ttctaacagt tttttattag agagcagatc tctgatgatc aaccaacgaa aaaagacggg    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
tttcatagca ttcttaagat ttctagccat acccccaaca gcaggaattt tggctagatg    300
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgcccccg    600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agttcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa gaaagatcat ggcttgtcca   1560
caaacaatgg tttctagact taccactgcc ttggacctct ggggcttcaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt ttttggaact gcatatggag ttttgtttag   2280
```

-continued cggagtttct tggaccatga aaataggaat agggattctg ctgacatggc taggattaaa 2340
ttcaaggaac acgtcccttt cgatgatgtg catcgcagtt ggcatggtca cactgtacct 2400
aggagtcatg gttcaggcag attcgggatg tgtaatcaac tggaaaggca gagaacttaa 2460
atgtggaagc ggcatttttg tcactaatga agttcacact tggacagagc aatacaaatt 2520
ccaggctgac tcccccaaga gactatcagc agccattggg aaggcatggg aggagggtgt 2580
gtgtggaatc cgatcagcca ctcgtctcga gaacatcatg tggaaacaaa tatcaaatga 2640
attgaaccac atcctacttg aaaatgacat gaaatttaca gtggtcgtgg gagatgttag 2700
tggaatcttg gcccaaggga aaaaaatgat taggccacaa cccatggaac acaaatactc 2760
gtggaaaagc tggggaaaag ccaaaatcat aggagcggat gtacagaaca ccaccttcat 2820
catcgacggc ccaaacaccc cagaatgccc tgacaatcaa agagcatgga atatttggga 2880
agtagaggac tatggatttg ggattttcac gacaaacata tggttgaaat tgcgtgactc 2940
ctacacccaa gtatgtgacc accggctgat gtcagctgcc attaaggaca gcaaggcagt 3000
ccatgctgac atggggtact ggatagaaag tgaaaagaac gagacatgga agttggcgag 3060
agcctccttt atagaagtta agacatgcat ctggccaaaa tcccacactc tatggagcaa 3120
tggagttctg gaaagtgaaa tgataattcc aaagatatat ggaggaccaa tatctcagca 3180
caactacaga ccaggatatt tcacacaaac agcagggccg tggcacctag gcaagttgga 3240
actagatttc gatttttgtg aaggtaccac agttgttgtg gatgaacatt gtggaaatcg 3300
aggaccatct ctcagaacca caacagtcac aggaaagata atccatgaat ggtgctgcag 3360
atcttgtacg ctacccccc tacgtttcaa aggggaagac gggtgttggt acggcatgga 3420
aatcagacca gtgaaggaca aggaagagaa cctggtcaag tcaatggtct ctgcagggtc 3480
aggagaagtg gacagctttt cactaggact gctatgcata tcaataatga ttgaagaagt 3540
gatgagatcc agatggagca aaaaaatgct gatgactgga acactggctg tgttcctcct 3600
tcttataatg ggacaattga catggagtga tctgatcagg ttatgtatta tggttggagc 3660
caacgcttca gacaagatgg ggatgggaac aacgtaccta gctttaatgg ccactttcaa 3720
aatgagacca atgttcgccg tcgggctatt atttcgcaga ctaacatcta gagaagttct 3780
tcttcttaca attggcttga gcctggtggc atccgtggag ctaccaagtt ccctagagga 3840
gctgggggat ggacttgcaa taggcatcat gatgttgaaa ttattgactg attttcagtc 3900
acaccagcta tgggctactc tgctatcctt gacatttatt aaaacaactt tttcattgca 3960
ctatgcatgg aagacaatgg ctatggtact gtcaattgta tctctcttcc ctttatgcct 4020
gtccacgacc tctcaaaaaa caacatggct tccggtgctg ttgggatctc ttggatgcaa 4080
accactaccc atgtttctta taacagaaaa caaaatctgg ggaaggaaga gttggcccct 4140
caatgaagga attatggctg ttggaatagt tagtattcta ctaagttcac ttttaaaaaa 4200
tgatgtgccg ctagccggcc cattaatagc tggaggcatg ctaatagcat gttatgtcat 4260
atccggaagc tcagctgatt tatcactgga gaaagcggct gaggtctcct gggaggaaga 4320
agcagaacac tcaggcgcct cacacaacat actagtagag gttcaagatg atggaaccat 4380
gaagataaaa gatgaagaga gagatgacac gctcaccatt ctccttaaag caactctgct 4440
ggcagtctca ggggtgtacc caatgtcaat accagcgacc ctttttgtgt ggtatttttg 4500
gcagaaaaag aaacagagat caggagtgct atgggacaca cccagccccc cagaagtgga 4560
aagagcagtt cttgatgatg gcatctatag aattttgcaa agaggactgt tgggcaggtc 4620
ccaagtagga gtaggagttt tccaagaagg cgtgttccac acaatgtggc acgtcactag 4680

-continued

```
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acgaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctatg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcatgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
```

-continued

```
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacaa ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac acccttttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
```

-continued

```
ccaactgata agacaaatgg agtccgaggg aatcttttta cccagcgaat tggaaacccc   9480

aaatctagcc ggaagagttc tcgactggtt ggaaaaatat ggtgtcgaaa ggctgaaaag   9540

aatggcaatc agcggagatg actgtgtggt gaaaccaatt gatgacaggt tcgcaacagc   9600

cttaacagct ttgaatgaca tgggaaaagt aagaaaagac ataccacaat gggaaccttc   9660

aaaaggatgg aatgattggc aacaagtgcc tttctgttca caccacttcc accagctaat   9720

tatgaaggat gggagggaga tagtggtgcc atgccgcaac caagatgaac ttgtggggag   9780

ggccagagta tcacaaggcg ccggatggag cctgagagaa accgcatgcc taggcaagtc   9840

atatgcacaa atgtggcagc tgatgtattt ccacaggaga gacctgagac tggcggctaa   9900

cgctatttgt tcagccgttc cagttgattg ggtcccaacc agccgcacca cctggtcgat   9960

ccatgcccat caccaatgga tgacaacaga agacatgtta tcagtatgga atagggtctg  10020

gatagaggaa aacccatgga tggaggataa gactcatgtg tccagttggg aagaagttcc  10080

atacctagga aagagggaag atcagtggtg tggatccctg ataggcttaa cagcaagggc  10140

cacctgggcc actaatatac aagtggccat aaaccaagtg agaaggctca ttgggaatga  10200

gaattatcta gattacatga catcaatgaa gagattcaag aatgagagtg atcccgaagg  10260

ggcactctgg taagtcaaca cattcacaaa ataaaggaaa ataaaaaatc aaatgaggca  10320

agaagtcagg ccagattaag ccatagtacg gtaagagcta tgctgcctgt gagccccgtc  10380

caaggacgta aaatgaagtc aggccgaaag ccacggtttg agcaagccgt gctgcctgtg  10440

gctccatcgt ggggatgtaa aaacccggga ggctgcaacc catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcgt  10620

aacaataaac agcatattga cgctgggaga gaccagagat cctgctgtct ctacagcatc  10680

attccaggca cagaacgcca gaaaatggaa tggtgctgtt gaatcaacag gttct       10735
```

```
<210> SEQ ID NO 3
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: LAV-1
      Dengue virus type 1 strain 16007 (PDK-13) polyprotein precursor,
      complete cds

<400> SEQUENCE: 3
```

```
agttgttagt ctacgtggac cgacaagaac agtttcgaat cggaagcttg cttaacgtag     60

ttctaacagt tttttattag agagcagatc tctgatgatc aaccaacgaa aaaagacggg    120

tcgaccgtct ttcaatatgc tgaaacgcgc gagaaaccgc gtgtcaactg tttcacagtt    180

ggcgaagaga ttctcaaaag gattgctctc aggccaagga cccatgaaat tggtgatggc    240

tttcatagca ttcttaagat ttctagccat acccccaaca gcaggaattt tggctagatg    300

gggctcattc aagaagaatg gagcgattaa agtgttacgg ggtttcaaga gagaaatctc    360

aaacatgcta aacataatga acaggaggaa aagatccgtg accatgctcc ttatgctgct    420

gcccacagcc ctggcgttcc atctgacgac acgaggggga gagccgcata tgatagttag    480

caagcaggaa agaggaaagt cacttttgtt caagacctct gcaggtgtca acatgtgcac    540

cctcattgcg atggatttgg gagagttgtg tgaggacacg atgacctaca aatgccccg    600
```

-continued

```
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agctcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa aagaaatcat ggcttgtcca   1560
caaacagtgg tttctagact taccactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt tttggaact gcatatggag ttttgtttag   2280
cggagtttct tggaccatga aaataggaat agggattctg ctgacatggc taggattaaa   2340
ttcaaggaac acgtcccttt cggtgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg gagacgttag   2700
tggaatcttg gcccaaggga aaaaaatgat taggccacaa cccatggaac acaaatactc   2760
gtggaaaagc tggggaaaag ctaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
```

-continued

```
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
atcttgtacg ctacccccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
```

-continued gagagttccc aattataaca tgattatcat ggatgaagca cacttcaccg atccagccag 5400
catagcagcc agagggtaca tctcaacccg agtgggtatg ggtgaagcag ctgcgatctt 5460
tatgacagcc actcccccag gatcggtgga ggcctttcca cagagcaatg caattatcca 5520
agatgaggaa agagacattc ctgagagatc atggaactca ggctatgact ggatcactga 5580
ttttccaggt aaaacagtct ggtttgttcc aagcatcaaa tcaggaaatg acattgccaa 5640
ctgtttaaga aaaaacggga aacgggtgat ccaattgagc agaaaaacct ttgacactga 5700
gtaccagaaa acaaaaaaca acgactggga ctatgtcgtc acaacagaca tttccgaaat 5760
gggagcaaat ttccgggccg acagggtaat agacccaagg cggtgtctga aaccggtaat 5820
actaaaagat ggtccagagc gcgtcattct agccggaccg atgccagtga ctgtggccag 5880
tgccgcccag aggagaggaa gaattggaag gaaccaaaac aaggaaggtg atcagtatat 5940
ttacatggga cagcctttaa acaatgatga ggaccacgct cattggacag aagcaaagat 6000
gctccttgac aatataaaca caccagaagg gattatccca gccctctttg agccggagag 6060
agaaaagagt gcagctatag acggggaata cagactgcgg ggtgaagcaa ggaaaacgtt 6120
cgtggagctc atgagaagag gggatctacc agtctggcta tcctacaaag ttgcctcaga 6180
aggcttccag tactccgaca gaaggtggtg cttcgatggg gaaaggaaca accaggtgtt 6240
ggaggagaac atggacgtgg agatctggac aaaagaagga gaaagaaaga aactacgacc 6300
tcgctggttg gacgccagaa catactctga cccactggct ctgcgcgagt ttaaagagtt 6360
tgcagcagga agaagaagcg tctcaggtga cctaatatta gaaataggga aacttccaca 6420
acatttgacg caaagggccc agaatgcttt ggacaacttg gtcatgttgc acaattccga 6480
acaaggagga aaagcctata gacatgctat ggaagaactg ccagacacaa tagaaacgtt 6540
gatgctccta gccttgatag ctgtgttgac tggtggagtg acgctgttct tcctatcagg 6600
aagaggtcta ggaaaaacat ctatcggctt actctgcgtg atggcctcaa gcgcactgtt 6660
atggatggcc agtgtggagc cccattggat agcggcctcc atcatactgg agttctttct 6720
gatggtactg cttattccag agccagacag acagcgcact ccacaggaca accagctagc 6780
atatgtggtg ataggtctgt tattcgtgat attgacagtg gcagccaatg agatgggatt 6840
attggaaacc acaaagaaag acctggggat tggccatgta gctgctgaaa accaccacca 6900
tgctacaatg ctggacgtag acctacatcc agcttcagcc tggaccctct atgcagtggc 6960
cacaacaatc atcactccta tgatgagaca cacaattgaa aacacaacgg caaatatttc 7020
cctgacagcc atcgcaaacc aagcagctat attgatggga cttgacaagg gatggccaat 7080
atcgaagatg gacataggag ttccacttct cgccttgggg tgctattccc aagtgaatcc 7140
gctgacactg atagcggcag tattgatgct agtagctcat tacgccataa ttggacctgg 7200
actgcaagca aaagctacta gagaagctca aaaaagaaca gcggctggaa taatgaaaaa 7260
tccaactgtc gacgggattg ttgcaataga cttagatccc gtggtttacg atgcaaaatt 7320
tgaaaaacag ctaggccaaa taatgttgtt gatactttgc acatcacaga ttcttttgat 7380
gcggactaca tgggccttgt gtgaatccat cacattggct actggacctc tgaccactct 7440
ttgggaggga tctccaggaa aattctggaa caccacaata gcggtatcca tggcaaacat 7500
tttcaggggg agttatctag caggagcagg tctggccttc tcattaatga aatctctagg 7560
aggaggtagg agaggcacgg gagcccaagg ggaaacactg ggagaaaaat ggaaaagaca 7620
actaaaccaa ctgagcaagt cagaattcaa tacttacaag aggagtggga ttatggaggt 7680
ggatagatcc gaagccaaag agggactgaa aagaggagaa acaaccaaac acgcagtatc 7740

-continued

```
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac acccctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga atagggtctg  10020
gatagaggaa aacccatgga tggaggataa gactcatgtg tccagttggg aagaagttcc  10080
```

-continued atacctagga aagagggaag atcagtggtg tggatccctg ataggcttaa cagcaagggc 10140
cacctgggcc actaatatac aagtggccat aaaccaagtg agaaggctca ttgggaatga 10200
gaattatcta gattacatga catcaatgaa gagattcaag aatgagagtg atcccgaagg 10260
ggcactctgg taagtcaaca cattcacaaa ataaaggaaa ataaaaaatc aaatgaggca 10320
agaagtcagg ccagattaag ccatagtacg gtaagagcta tgctgcctgt gagccccgtc 10380
caaggacgta aaatgaagtc aggccgaaag ccacggtttg agcaagccgt gctgcctgtg 10440
gctccatcgt ggggatgtaa aaacccggga ggctgcaacc catggaagct gtacgcatgg 10500
ggtagcagac tagtggttag aggagacccc tcccaagaca caacgcagca gcggggccca 10560
acaccagggg aagctgtacc ctggtggtaa ggactagagg ttagaggaga ccccccgcgt 10620
aacaataaac agcatattga cgctgggaga gaccagagat cctgctgtct ctacagcatc 10680
attccaggca cagaacgcca gaaaatggaa tggtgctgtt gaatcaacag gttct 10735

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4
gttttcccag tcacgactac gtggaccgac aagaacag 38

<210> SEQ ID NO 5
<211> LENGTH: 37
<212> TYPE: DNA
<213> ORGANISM: Artificial sequence
<220> FEATURE:
<223> OTHER INFORMATION: primer

<400> SEQUENCE: 5
aacagctatg accatgggat ggagttacca gcatcag 37

<210> SEQ ID NO 6
<211> LENGTH: 37
<212> TYPE: DNA
<213> ORGANISM: Artificial sequence
<220> FEATURE:
<223> OTHER INFORMATION: primer

<400> SEQUENCE: 6
gttttcccag tcacgactga acaccgacga gacaaac 37

<210> SEQ ID NO 7
<211> LENGTH: 36
<212> TYPE: DNA
<213> ORGANISM: Artificial sequence
<220> FEATURE:
<223> OTHER INFORMATION: primer

<400> SEQUENCE: 7
aacagctatg accatgaggt ccaaggcagt ggtaag 36

<210> SEQ ID NO 8
<211> LENGTH: 38
<212> TYPE: DNA
<213> ORGANISM: Artificial sequence
<220> FEATURE:
<223> OTHER INFORMATION: primer

<400> SEQUENCE: 8

-continued gttttcccag tcacgacttg gaaatgagac cacagaac 38

<210> SEQ ID NO 9
<211> LENGTH: 36
<212> TYPE: DNA
<213> ORGANISM: Artificial sequence
<220> FEATURE:
<223> OTHER INFORMATION: primer

<400> SEQUENCE: 9
aacagctatg accatggaaa caccgctgaa caaaac 36

<210> SEQ ID NO 10
<211> LENGTH: 36
<212> TYPE: DNA
<213> ORGANISM: Artificial sequence
<220> FEATURE:
<223> OTHER INFORMATION: primer

<400> SEQUENCE: 10
gttttcccag tcacgacggt tcaagaaggg aagcag 36

<210> SEQ ID NO 11
<211> LENGTH: 37
<212> TYPE: DNA
<213> ORGANISM: Artificial sequence
<220> FEATURE:
<223> OTHER INFORMATION: primer

<400> SEQUENCE: 11
aacagctatg accatgttct atccagtacc ccatgtc 37

<210> SEQ ID NO 12
<211> LENGTH: 39
<212> TYPE: DNA
<213> ORGANISM: Artificial sequence
<220> FEATURE:
<223> OTHER INFORMATION: primer

<400> SEQUENCE: 12
gttttcccag tcacgaccag aataccacct tcatcatcg 39

<210> SEQ ID NO 13
<211> LENGTH: 35
<212> TYPE: DNA
<213> ORGANISM: Artificial sequence
<220> FEATURE:
<223> OTHER INFORMATION: primer

<400> SEQUENCE: 13
aacagctatg accatgttcc catccccatc ttgtc 35

<210> SEQ ID NO 14
<211> LENGTH: 39
<212> TYPE: DNA
<213> ORGANISM: Artificial sequence
<220> FEATURE:
<223> OTHER INFORMATION: primer

<400> SEQUENCE: 14
gttttcccag tcacgacgga aatcagacca gtcaaggag 39

<210> SEQ ID NO 15
<211> LENGTH: 36
<212> TYPE: DNA

-continued

<213> ORGANISM: Artificial sequence
<220> FEATURE:
<223> OTHER INFORMATION: primer

<400> SEQUENCE: 15
aacagctatg accatgtgtt gtgtgaggca ccagag 36

<210> SEQ ID NO 16
<211> LENGTH: 38
<212> TYPE: DNA
<213> ORGANISM: Artificial sequence
<220> FEATURE:
<223> OTHER INFORMATION: primer

<400> SEQUENCE: 16
gttttcccag tcacgacgca aaccactaac catgtttc 38

<210> SEQ ID NO 17
<211> LENGTH: 35
<212> TYPE: DNA
<213> ORGANISM: Artificial sequence
<220> FEATURE:
<223> OTHER INFORMATION: primer

<400> SEQUENCE: 17
aacagctatg accatgccac ttgttgtcac cactc 35

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18
gttttcccag tcacgaccca agggaagaga ctggaac 37

<210> SEQ ID NO 19
<211> LENGTH: 37
<212> TYPE: DNA
<213> ORGANISM: Artificial sequence
<220> FEATURE:
<223> OTHER INFORMATION: primer

<400> SEQUENCE: 19
aacagctatg accatgtcct gatttgatgc ttggaac 37

<210> SEQ ID NO 20
<211> LENGTH: 38
<212> TYPE: DNA
<213> ORGANISM: Artificial sequence
<220> FEATURE:
<223> OTHER INFORMATION: primer

<400> SEQUENCE: 20
gttttcccag tcacgacaag cacattttac cgatccag 38

<210> SEQ ID NO 21
<211> LENGTH: 41
<212> TYPE: DNA
<213> ORGANISM: Artificial sequence
<220> FEATURE:
<223> OTHER INFORMATION: primer

<400> SEQUENCE: 21
aacagctatg accatggtcg tagtttcttt ctttctcctt c 41

-continued

<210> SEQ ID NO 22
<211> LENGTH: 37
<212> TYPE: DNA
<213> ORGANISM: Artificial sequence
<220> FEATURE:
<223> OTHER INFORMATION: primer

<400> SEQUENCE: 22
gttttcccag tcacgacgca atagacgggg aatacag 37

<210> SEQ ID NO 23
<211> LENGTH: 36
<212> TYPE: DNA
<213> ORGANISM: Artificial sequence
<220> FEATURE:
<223> OTHER INFORMATION: primer

<400> SEQUENCE: 23
aacagctatg accatgatga tggtggtttt cagcag 36

<210> SEQ ID NO 24
<211> LENGTH: 37
<212> TYPE: DNA
<213> ORGANISM: Artificial sequence
<220> FEATURE:
<223> OTHER INFORMATION: primer

<400> SEQUENCE: 24
gttttcccag tcacgacgtg ttgcttattc cagagcc 37

<210> SEQ ID NO 25
<211> LENGTH: 38
<212> TYPE: DNA
<213> ORGANISM: Artificial sequence
<220> FEATURE:
<223> OTHER INFORMATION: primer

<400> SEQUENCE: 25
aacagctatg accatggctg tcttttccat ttttctcc 38

<210> SEQ ID NO 26
<211> LENGTH: 37
<212> TYPE: DNA
<213> ORGANISM: Artificial sequence
<220> FEATURE:
<223> OTHER INFORMATION: primer

<400> SEQUENCE: 26
gttttcccag tcacgacact ttgcacatca cagatcc 37

<210> SEQ ID NO 27
<211> LENGTH: 35
<212> TYPE: DNA
<213> ORGANISM: Artificial sequence
<220> FEATURE:
<223> OTHER INFORMATION: primer

<400> SEQUENCE: 27
aacagctatg accatgttcg cactagcatt cctcc 35

<210> SEQ ID NO 28
<211> LENGTH: 37
<212> TYPE: DNA
<213> ORGANISM: Artificial sequence
<220> FEATURE:

-continued

<223> OTHER INFORMATION: primer

<400> SEQUENCE: 28
gttttcccag tcacgaccac ctgagaaatg tgacacc 37

<210> SEQ ID NO 29
<211> LENGTH: 38
<212> TYPE: DNA
<213> ORGANISM: Artificial sequence
<220> FEATURE:
<223> OTHER INFORMATION: primer

<400> SEQUENCE: 29
aacagctatg accatgtttc cttgtttatg aagctccc 38

<210> SEQ ID NO 30
<211> LENGTH: 36
<212> TYPE: DNA
<213> ORGANISM: Artificial sequence
<220> FEATURE:
<223> OTHER INFORMATION: primer

<400> SEQUENCE: 30
gttttcccag tcacgaccaa aagcgaaacg aggcac 36

<210> SEQ ID NO 31
<211> LENGTH: 38
<212> TYPE: DNA
<213> ORGANISM: Artificial sequence
<220> FEATURE:
<223> OTHER INFORMATION: primer

<400> SEQUENCE: 31
aacagctatg accatggttt caccacacag tcatctcc 38

<210> SEQ ID NO 32
<211> LENGTH: 37
<212> TYPE: DNA
<213> ORGANISM: Artificial sequence
<220> FEATURE:
<223> OTHER INFORMATION: primer

<400> SEQUENCE: 32
gttttcccag tcacgacaga ccagcgaaaa atggaac 37

<210> SEQ ID NO 33
<211> LENGTH: 35
<212> TYPE: DNA
<213> ORGANISM: Artificial sequence
<220> FEATURE:
<223> OTHER INFORMATION: primer

<400> SEQUENCE: 33
aacagctatg accatgtccc aatgagcctt ctcac 35

<210> SEQ ID NO 34
<211> LENGTH: 38
<212> TYPE: DNA
<213> ORGANISM: Artificial sequence
<220> FEATURE:
<223> OTHER INFORMATION: primer

<400> SEQUENCE: 34
gttttcccag tcacgacgct aatgctatct gttcagcc 38

-continued

<210> SEQ ID NO 35
<211> LENGTH: 36
<212> TYPE: DNA
<213> ORGANISM: Artificial sequence
<220> FEATURE:
<223> OTHER INFORMATION: primer
<400> SEQUENCE: 35
aacagctatg accatgtgat tcaacagcac cattcc 36

<210> SEQ ID NO 36
<211> LENGTH: 17
<212> TYPE: DNA
<213> ORGANISM: Artificial sequence
<220> FEATURE:
<223> OTHER INFORMATION: primer
<400> SEQUENCE: 36
ccatggaagc tgtacgc 17

<210> SEQ ID NO 37
<211> LENGTH: 19
<212> TYPE: DNA
<213> ORGANISM: Artificial sequence
<220> FEATURE:
<223> OTHER INFORMATION: primer
<400> SEQUENCE: 37
gagacagcag gatctctgg 19

<210> SEQ ID NO 38
<211> LENGTH: 17
<212> TYPE: DNA
<213> ORGANISM: Artificial sequence
<220> FEATURE:
<223> OTHER INFORMATION: primer tail
<400> SEQUENCE: 38
gttttcccag tcacgac 17

<210> SEQ ID NO 39
<211> LENGTH: 16
<212> TYPE: DNA
<213> ORGANISM: Artificial sequence
<220> FEATURE:
<223> OTHER INFORMATION: primer tail
<400> SEQUENCE: 39
aacagctatg accatg 16

<210> SEQ ID NO 40
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: VDV2
<220> FEATURE:
<221> NAME/KEY: misc_feature
<222> LOCATION: (10361)..(10361)
<223> OTHER INFORMATION: n=A or T or G or C
<400> SEQUENCE: 40
agttgttagt ctacgtggac cgacaaagac agattctttg agggagctaa gctcaatgta 60
gttctaacag ttttttaatt agagagcaga tctctgatga ataaccaacg gaaaaaggcg 120

-continued

```
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
agcagacaag agaaagggaa aagtcttctg tttaaaacag aggttggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgcgaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaagag   1620
tcaaattgga tacagaagga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccctttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaaa   2520
```

-continued

```
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac caacatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
```

-continued

```
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tcacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
```

-continued

```
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa aaatcacact agaagaccta aaaaatgaag agatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
```

-continued

```
ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aaacatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc naggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagggga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                   10723
```

```
<210> SEQ ID NO 41
<211> LENGTH: 3392
<212> TYPE: PRT
<213> ORGANISM: Dengue virus
<220> FEATURE:
<221> NAME/KEY: CHAIN
<222> LOCATION: (1)..(114)
<223> OTHER INFORMATION: capsid protein
<220> FEATURE:
<221> NAME/KEY: CHAIN
<222> LOCATION: (115)..(280)
<223> OTHER INFORMATION: premembrane protein
<220> FEATURE:
<221> NAME/KEY: CHAIN
<222> LOCATION: (281)..(775)
<223> OTHER INFORMATION: envelope glycoprotein
<220> FEATURE:
<221> NAME/KEY: CHAIN
<222> LOCATION: (776)..(1127)
<223> OTHER INFORMATION: nonstructural protein 1
<220> FEATURE:
<221> NAME/KEY: CHAIN
<222> LOCATION: (1128)..(1345)
<223> OTHER INFORMATION: nonstructural protein 2A
<220> FEATURE:
<221> NAME/KEY: CHAIN
<222> LOCATION: (1346)..(1475)
<223> OTHER INFORMATION: nonstructural protein 2B
<220> FEATURE:
<221> NAME/KEY: CHAIN
<222> LOCATION: (1476)..(2094)
<223> OTHER INFORMATION: nonstructural protein 3
<220> FEATURE:
<221> NAME/KEY: CHAIN
<222> LOCATION: (2095)..(2244)
<223> OTHER INFORMATION: nonstructural protein 4A
<220> FEATURE:
<221> NAME/KEY: CHAIN
<222> LOCATION: (2245)..(2493)
<223> OTHER INFORMATION: nonstructural protein 4B
```

-continued

<220> FEATURE:
<221> NAME/KEY: CHAIN
<222> LOCATION: (2494)..(3392)
<223> OTHER INFORMATION: nonstructural protein 5

<400> SEQUENCE: 41

```
Met Ile Asn Gln Arg Lys Lys Thr Gly Arg Pro Ser Phe Asn Met Leu
1               5                   10                  15

Lys Arg Ala Arg Asn Arg Val Ser Thr Val Ser Gln Leu Ala Lys Arg
            20                  25                  30

Phe Ser Lys Gly Leu Leu Ser Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Ile Leu Ala Arg Trp Gly Ser Phe Lys Lys Asn Gly Ala Ile Lys Val
65                  70                  75                  80

Leu Arg Gly Phe Lys Arg Glu Ile Ser Asn Met Leu Asn Ile Met Asn
                85                  90                  95

Arg Arg Lys Arg Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380
```

-continued

```
Cys Gly Leu Phe Gly Lys Gly Ser Leu Ile Thr Cys Ala Lys Phe Lys
385                 390                 395                 400

Cys Val Thr Lys Leu Glu Gly Lys Ile Ala Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Lys Lys Ser Trp Leu Val His Lys Gln Trp Phe Leu Asp Leu
                485                 490                 495

Pro Leu Pro Trp Thr Ser Gly Ala Leu Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Val Met Cys Ile Ala Val Gly Met Val Thr Leu Tyr
        755                 760                 765

Leu Gly Val Met Val Gln Ala Asp Ser Gly Cys Val Ile Asn Trp Lys
    770                 775                 780

Gly Arg Glu Leu Lys Cys Gly Ser Gly Ile Phe Val Thr Asn Glu Val
785                 790                 795                 800

His Thr Trp Thr Glu Gln Tyr Lys Phe Gln Ala Asp Ser Pro Lys Arg
```

-continued

```
                805                 810                 815

Leu Ser Ala Ala Ile Gly Lys Ala Trp Glu Glu Gly Val Cys Gly Ile
            820                 825                 830

Arg Ser Ala Thr Arg Leu Glu Asn Ile Met Trp Lys Gln Ile Ser Asn
        835                 840                 845

Glu Leu Asn His Ile Leu Leu Glu Asn Asp Met Lys Phe Thr Val Val
    850                 855                 860

Val Gly Asp Val Ser Gly Ile Leu Ala Gln Gly Lys Lys Met Ile Arg
865                 870                 875                 880

Pro Gln Pro Met Glu His Lys Tyr Ser Trp Lys Ser Trp Gly Lys Ala
                885                 890                 895

Lys Ile Ile Gly Ala Asp Val Gln Asn Thr Thr Phe Ile Ile Asp Gly
            900                 905                 910

Pro Asn Thr Pro Glu Cys Pro Asp Asn Gln Arg Ala Trp Asn Ile Trp
        915                 920                 925

Glu Val Glu Asp Tyr Gly Phe Gly Ile Phe Thr Thr Asn Ile Trp Leu
    930                 935                 940

Lys Leu Arg Asp Ser Tyr Thr Gln Val Cys Asp His Arg Leu Met Ser
945                 950                 955                 960

Ala Ala Ile Lys Asp Ser Lys Ala Val His Ala Asp Met Gly Tyr Trp
                965                 970                 975

Ile Glu Ser Glu Lys Asn Glu Thr Trp Lys Leu Ala Arg Ala Ser Phe
            980                 985                 990

Ile Glu Val Lys Thr Cys Ile Trp  Pro Lys Ser His Thr  Leu Trp Ser
        995                 1000                1005

Asn Gly  Val Leu Glu Ser Glu  Met Ile Ile Pro Lys  Ile Tyr Gly
    1010                 1015                 1020

Gly Pro  Ile Ser Gln His Asn  Tyr Arg Pro Gly Tyr  Phe Thr Gln
    1025                 1030                 1035

Thr Ala  Gly Pro Trp His Leu  Gly Lys Leu Glu Leu  Asp Phe Asp
    1040                 1045                 1050

Phe Cys  Glu Gly Thr Thr Val  Val Val Asp Glu His  Cys Gly Asn
    1055                 1060                 1065

Arg Gly  Pro Ser Leu Arg Thr  Thr Thr Val Thr Gly  Lys Ile Ile
    1070                 1075                 1080

His Glu  Trp Cys Cys Arg Ser  Cys Thr Leu Pro Pro  Leu Arg Phe
    1085                 1090                 1095

Lys Gly  Glu Asp Gly Cys Trp  Tyr Gly Met Glu Ile  Arg Pro Val
    1100                 1105                 1110

Lys Asp  Lys Glu Glu Asn Leu  Val Lys Ser Met Val  Ser Ala Gly
    1115                 1120                 1125

Ser Gly  Glu Val Asp Ser Phe  Ser Leu Gly Leu Leu  Cys Ile Ser
    1130                 1135                 1140

Ile Met  Ile Glu Glu Val Met  Arg Ser Arg Trp Ser  Lys Lys Met
    1145                 1150                 1155

Leu Met  Thr Gly Thr Leu Ala  Val Phe Leu Leu Leu  Ile Met Gly
    1160                 1165                 1170

Gln Leu  Thr Trp Ser Asp Leu  Ile Arg Leu Cys Ile  Met Val Gly
    1175                 1180                 1185

Ala Asn  Ala Ser Asp Lys Met  Gly Met Gly Thr Thr  Tyr Leu Ala
    1190                 1195                 1200

Leu Met  Ala Thr Phe Lys Met  Arg Pro Met Phe Ala  Val Gly Leu
    1205                 1210                 1215
```

-continued

```
Leu Phe Arg Arg Leu Thr Ser Arg Glu Val Leu Leu Leu Thr Ile
    1220                1225                1230

Gly Leu Ser Leu Val Ala Ser Val Glu Leu Pro Ser Ser Leu Glu
    1235                1240                1245

Glu Leu Gly Asp Gly Leu Ala Ile Gly Ile Met Met Leu Lys Leu
    1250                1255                1260

Leu Thr Asp Phe Gln Ser His Gln Leu Trp Ala Thr Leu Leu Ser
    1265                1270                1275

Leu Thr Phe Ile Lys Thr Thr Phe Ser Leu His Tyr Ala Trp Lys
    1280                1285                1290

Thr Met Ala Met Val Leu Ser Ile Val Ser Leu Phe Pro Leu Cys
    1295                1300                1305

Leu Ser Thr Thr Ser Gln Lys Thr Thr Trp Leu Pro Val Leu Leu
    1310                1315                1320

Gly Ser Leu Gly Cys Lys Pro Leu Pro Met Phe Leu Ile Thr Glu
    1325                1330                1335

Asn Lys Ile Trp Gly Arg Lys Ser Trp Pro Leu Asn Glu Gly Ile
    1340                1345                1350

Met Ala Val Gly Ile Val Ser Ile Leu Leu Ser Ser Leu Leu Lys
    1355                1360                1365

Asn Asp Val Pro Leu Ala Gly Pro Leu Ile Ala Gly Gly Met Leu
    1370                1375                1380

Ile Ala Cys Tyr Val Ile Ser Gly Ser Ser Ala Asp Leu Ser Leu
    1385                1390                1395

Glu Lys Ala Ala Glu Val Ser Trp Glu Glu Glu Ala Glu His Ser
    1400                1405                1410

Gly Ala Ser His Asn Ile Leu Val Glu Val Gln Asp Asp Gly Thr
    1415                1420                1425

Met Lys Ile Lys Asp Glu Glu Arg Asp Asp Thr Leu Thr Ile Leu
    1430                1435                1440

Leu Lys Ala Thr Leu Leu Ala Val Ser Gly Val Tyr Pro Met Ser
    1445                1450                1455

Ile Pro Ala Thr Leu Phe Val Trp Tyr Phe Trp Gln Lys Lys Lys
    1460                1465                1470

Gln Arg Ser Gly Val Leu Trp Asp Thr Pro Ser Pro Pro Glu Val
    1475                1480                1485

Glu Arg Ala Val Leu Asp Asp Gly Ile Tyr Arg Ile Leu Gln Arg
    1490                1495                1500

Gly Leu Leu Gly Arg Ser Gln Val Gly Val Gly Val Phe Gln Glu
    1505                1510                1515

Gly Val Phe His Thr Met Trp His Val Thr Arg Gly Ala Val Leu
    1520                1525                1530

Met Tyr Gln Gly Lys Arg Leu Glu Pro Ser Trp Ala Ser Val Lys
    1535                1540                1545

Lys Asp Leu Ile Ser Tyr Gly Gly Gly Trp Arg Phe Gln Gly Ser
    1550                1555                1560

Trp Asn Thr Gly Glu Glu Val Gln Val Ile Ala Val Glu Pro Gly
    1565                1570                1575

Lys Asn Pro Lys Asn Val Gln Thr Thr Pro Gly Thr Phe Lys Thr
    1580                1585                1590

Pro Glu Gly Glu Val Gly Ala Ile Ala Leu Asp Phe Lys Pro Gly
    1595                1600                1605
```

-continued

```
Thr Ser  Gly Ser Pro Ile Val  Asn Arg Glu Gly Lys  Ile Val Gly
    1610                 1615                 1620

Leu Tyr  Gly Asn Gly Val Val  Thr Thr Ser Gly Thr  Tyr Val Ser
    1625                 1630                 1635

Ala Ile  Ala Gln Ala Lys Ala  Ser Gln Glu Gly Pro  Leu Pro Glu
    1640                 1645                 1650

Ile Glu  Asp Lys Val Phe Arg  Lys Arg Asn Leu Thr  Ile Met Asp
    1655                 1660                 1665

Leu His  Pro Gly Ser Gly Lys  Thr Arg Arg Tyr Leu  Pro Ala Ile
    1670                 1675                 1680

Val Arg  Glu Ala Ile Lys Arg  Lys Leu Arg Thr Leu  Ile Leu Ala
    1685                 1690                 1695

Pro Thr  Arg Val Val Ala Ser  Glu Met Ala Glu Ala  Leu Lys Gly
    1700                 1705                 1710

Val Pro  Ile Arg Tyr Gln Thr  Thr Ala Val Lys Ser  Glu His Thr
    1715                 1720                 1725

Gly Lys  Glu Ile Val Asp Leu  Met Cys His Ala Thr  Phe Thr Met
    1730                 1735                 1740

Arg Leu  Leu Ser Pro Val Arg  Val Pro Asn Tyr Asn  Met Ile Ile
    1745                 1750                 1755

Met Asp  Glu Ala His Phe Thr  Asp Pro Ala Ser Ile  Ala Ala Arg
    1760                 1765                 1770

Gly Tyr  Ile Ser Thr Arg Val  Gly Met Gly Glu Ala  Ala Ala Ile
    1775                 1780                 1785

Phe Met  Thr Ala Thr Pro Pro  Gly Ser Val Glu Ala  Phe Pro Gln
    1790                 1795                 1800

Ser Asn  Ala Ile Ile Gln Asp  Glu Glu Arg Asp Ile  Pro Glu Arg
    1805                 1810                 1815

Ser Trp  Asn Ser Gly Tyr Asp  Trp Ile Thr Asp Phe  Pro Gly Lys
    1820                 1825                 1830

Thr Val  Trp Phe Val Pro Ser  Ile Lys Ser Gly Asn  Asp Ile Ala
    1835                 1840                 1845

Asn Cys  Leu Arg Lys Asn Gly  Lys Arg Val Ile Gln  Leu Ser Arg
    1850                 1855                 1860

Lys Thr  Phe Asp Thr Glu Tyr  Gln Lys Thr Lys Asn  Asn Asp Trp
    1865                 1870                 1875

Asp Tyr  Val Val Thr Thr Asp  Ile Ser Glu Met Gly  Ala Asn Phe
    1880                 1885                 1890

Arg Ala  Asp Arg Val Ile Asp  Pro Arg Arg Cys Leu  Lys Pro Val
    1895                 1900                 1905

Ile Leu  Lys Asp Gly Pro Glu  Arg Val Ile Leu Ala  Gly Pro Met
    1910                 1915                 1920

Pro Val  Thr Val Ala Ser Ala  Ala Gln Arg Arg Gly  Arg Ile Gly
    1925                 1930                 1935

Arg Asn  Gln Asn Lys Glu Gly  Asp Gln Tyr Ile Tyr  Met Gly Gln
    1940                 1945                 1950

Pro Leu  Lys Asn Asp Glu Asp  His Ala His Trp Thr  Glu Ala Lys
    1955                 1960                 1965

Met Leu  Leu Asp Asn Ile Asn  Thr Pro Glu Gly Ile  Ile Pro Ala
    1970                 1975                 1980

Leu Phe  Glu Pro Glu Arg Glu  Lys Ser Ala Ala Ile  Asp Gly Glu
    1985                 1990                 1995

Tyr Arg  Leu Arg Gly Glu Ala  Arg Lys Thr Phe Val  Glu Leu Met
```

-continued

```
    2000                2005                2010

Arg Arg  Gly Asp Leu Pro Val  Trp Leu Ser Tyr Lys  Val Ala Ser
    2015                2020                2025

Glu Gly  Phe Gln Tyr Ser Asp  Arg Arg Trp Cys Phe  Asp Gly Glu
    2030                2035                2040

Arg Asn  Asn Gln Val Leu Glu  Glu Asn Met Asp Val  Glu Ile Trp
    2045                2050                2055

Thr Lys  Glu Gly Glu Arg Lys  Lys Leu Arg Pro Arg  Trp Leu Asp
    2060                2065                2070

Ala Arg  Thr Tyr Ser Asp Pro  Leu Ala Leu Arg Glu  Phe Lys Glu
    2075                2080                2085

Phe Ala  Ala Gly Arg Arg Ser  Val Ser Gly Asp Leu  Ile Leu Glu
    2090                2095                2100

Ile Gly  Lys Leu Pro Gln His  Leu Thr Gln Arg Ala  Gln Asn Ala
    2105                2110                2115

Leu Asp  Asn Leu Val Met Leu  His Asn Ser Glu Gln  Gly Gly Lys
    2120                2125                2130

Ala Tyr  Arg His Ala Met Glu  Glu Leu Pro Asp Thr  Ile Glu Thr
    2135                2140                2145

Leu Met  Leu Leu Ala Leu Ile  Ala Val Leu Thr Gly  Gly Val Thr
    2150                2155                2160

Leu Phe  Phe Leu Ser Gly Arg  Gly Leu Gly Lys Thr  Ser Ile Gly
    2165                2170                2175

Leu Leu  Cys Val Met Ala Ser  Ser Ala Leu Leu Trp  Met Ala Ser
    2180                2185                2190

Val Glu  Pro His Trp Ile Ala  Ala Ser Ile Ile Leu  Glu Phe Phe
    2195                2200                2205

Leu Met  Val Leu Leu Ile Pro  Glu Pro Asp Arg Gln  Arg Thr Pro
    2210                2215                2220

Gln Asp  Asn Gln Leu Ala Tyr  Val Val Ile Gly Leu  Leu Phe Val
    2225                2230                2235

Ile Leu  Thr Val Ala Ala Asn  Glu Met Gly Leu Leu  Glu Thr Thr
    2240                2245                2250

Lys Lys  Asp Leu Gly Ile Gly  His Val Ala Ala Glu  Asn His His
    2255                2260                2265

His Ala  Thr Met Leu Asp Val  Asp Leu His Pro Ala  Ser Ala Trp
    2270                2275                2280

Thr Leu  Tyr Ala Val Ala Thr  Thr Ile Ile Thr Pro  Met Met Arg
    2285                2290                2295

His Thr  Ile Glu Asn Thr Thr  Ala Asn Ile Ser Leu  Thr Ala Ile
    2300                2305                2310

Ala Asn  Gln Ala Ala Ile Leu  Met Gly Leu Asp Lys  Gly Trp Pro
    2315                2320                2325

Ile Ser  Lys Met Asp Ile Gly  Val Pro Leu Leu Ala  Leu Gly Cys
    2330                2335                2340

Tyr Ser  Gln Val Asn Pro Leu  Thr Leu Ile Ala Ala  Val Leu Met
    2345                2350                2355

Leu Val  Ala His Tyr Ala Ile  Ile Gly Pro Gly Leu  Gln Ala Lys
    2360                2365                2370

Ala Thr  Arg Glu Ala Gln Lys  Arg Thr Ala Ala Gly  Ile Met Lys
    2375                2380                2385

Asn Pro  Thr Val Asp Gly Ile  Val Ala Ile Asp Leu  Asp Pro Val
    2390                2395                2400
```

-continued

```
Val Tyr  Asp Ala Lys Phe Glu  Lys Gln Leu Gly Gln  Ile Met Leu
    2405                 2410                 2415

Leu Ile  Leu Cys Thr Ser Gln  Ile Leu Leu Met Arg  Thr Thr Trp
    2420                 2425                 2430

Ala Leu  Cys Glu Ser Ile Thr  Leu Ala Thr Gly Pro  Leu Thr Thr
    2435                 2440                 2445

Leu Trp  Glu Gly Ser Pro Gly  Lys Phe Trp Asn Thr  Thr Ile Ala
    2450                 2455                 2460

Val Ser  Met Ala Asn Ile Phe  Arg Gly Ser Tyr Leu  Ala Gly Ala
    2465                 2470                 2475

Gly Leu  Ala Phe Ser Leu Met  Lys Ser Leu Gly Gly  Gly Arg Arg
    2480                 2485                 2490

Gly Thr  Gly Ala Gln Gly Glu  Thr Leu Gly Glu Lys  Trp Lys Arg
    2495                 2500                 2505

Gln Leu  Asn Gln Leu Ser Lys  Ser Glu Phe Asn Thr  Tyr Lys Arg
    2510                 2515                 2520

Ser Gly  Ile Met Glu Val Asp  Arg Ser Glu Ala Lys  Glu Gly Leu
    2525                 2530                 2535

Lys Arg  Gly Glu Thr Thr Lys  His Ala Val Ser Arg  Gly Thr Ala
    2540                 2545                 2550

Lys Leu  Arg Trp Phe Val Glu  Arg Asn Leu Val Lys  Pro Glu Gly
    2555                 2560                 2565

Lys Val  Ile Asp Leu Gly Cys  Gly Arg Gly Gly Trp  Ser Tyr Tyr
    2570                 2575                 2580

Cys Ala  Gly Leu Lys Lys Val  Thr Glu Val Lys Gly  Tyr Thr Lys
    2585                 2590                 2595

Gly Gly  Pro Gly His Glu Glu  Pro Ile Pro Met Ala  Thr Tyr Gly
    2600                 2605                 2610

Trp Asn  Leu Val Arg Leu His  Ser Gly Lys Asp Val  Phe Phe Ile
    2615                 2620                 2625

Pro Pro  Glu Lys Cys Asp Thr  Leu Leu Cys Asp Ile  Gly Glu Ser
    2630                 2635                 2640

Ser Pro  Asn Pro Thr Ile Glu  Glu Gly Arg Thr Leu  Arg Val Leu
    2645                 2650                 2655

Lys Met  Val Glu Pro Trp Leu  Arg Gly Asn Gln Phe  Cys Ile Lys
    2660                 2665                 2670

Ile Leu  Asn Pro Tyr Met Pro  Ser Val Val Glu Thr  Leu Glu Gln
    2675                 2680                 2685

Met Gln  Arg Lys His Gly Gly  Met Leu Val Arg Asn  Pro Leu Ser
    2690                 2695                 2700

Arg Asn  Ser Thr His Glu Met  Tyr Trp Val Ser Cys  Gly Thr Gly
    2705                 2710                 2715

Asn Ile  Val Ser Ala Val Asn  Met Thr Ser Arg Met  Leu Leu Asn
    2720                 2725                 2730

Arg Phe  Thr Met Ala His Arg  Lys Pro Thr Tyr Glu  Arg Asp Val
    2735                 2740                 2745

Asp Leu  Gly Ala Gly Thr Arg  His Val Ala Val Glu  Pro Glu Val
    2750                 2755                 2760

Ala Asn  Leu Asp Ile Ile Gly  Gln Arg Ile Glu Asn  Ile Lys Asn
    2765                 2770                 2775

Glu His  Lys Ser Thr Trp His  Tyr Asp Glu Asp Asn  Pro Tyr Lys
    2780                 2785                 2790
```

-continued

```
Thr Trp  Ala Tyr His Gly Ser  Tyr Glu Val Lys Pro  Ser Gly Ser
    2795                 2800                 2805

Ala Ser  Ser Met Val Asn Gly  Val Val Arg Leu Leu  Thr Lys Pro
    2810                 2815                 2820

Trp Asp  Val Ile Pro Met Val  Thr Gln Ile Ala Met  Thr Asp Thr
    2825                 2830                 2835

Thr Pro  Phe Gly Gln Gln Arg  Val Phe Lys Glu Lys  Val Asp Thr
    2840                 2845                 2850

Arg Thr  Pro Lys Ala Lys Arg  Gly Thr Ala Gln Ile  Met Glu Val
    2855                 2860                 2865

Thr Ala  Arg Trp Leu Trp Gly  Phe Leu Ser Arg Asn  Lys Lys Pro
    2870                 2875                 2880

Arg Ile  Cys Thr Arg Glu Glu  Phe Thr Arg Lys Val  Arg Ser Asn
    2885                 2890                 2895

Ala Ala  Ile Gly Ala Val Phe  Val Asp Glu Asn Gln  Trp Asn Ser
    2900                 2905                 2910

Ala Lys  Glu Ala Val Glu Asp  Glu Arg Phe Trp Glu  Leu Val His
    2915                 2920                 2925

Arg Glu  Arg Glu Leu His Lys  Gln Gly Lys Cys Ala  Thr Cys Val
    2930                 2935                 2940

Tyr Asn  Met Met Gly Lys Arg  Glu Lys Lys Leu Gly  Glu Phe Gly
    2945                 2950                 2955

Lys Ala  Lys Gly Ser Arg Ala  Ile Trp Tyr Met Trp  Leu Gly Ala
    2960                 2965                 2970

Arg Phe  Leu Glu Phe Glu Ala  Leu Gly Phe Met Asn  Glu Asp His
    2975                 2980                 2985

Trp Phe  Ser Arg Glu Asn Ser  Leu Ser Gly Val Glu  Gly Glu Gly
    2990                 2995                 3000

Leu His  Lys Leu Gly Tyr Ile  Leu Arg Asp Ile Ser  Arg Ile Pro
    3005                 3010                 3015

Gly Gly  Asn Met Tyr Ala Asp  Asp Thr Ala Gly Trp  Asp Thr Arg
    3020                 3025                 3030

Ile Thr  Glu Asp Asp Leu Gln  Asn Glu Ala Lys Ile  Thr Asp Ile
    3035                 3040                 3045

Met Glu  Pro Glu His Ala Leu  Leu Ala Thr Ser Ile  Phe Lys Leu
    3050                 3055                 3060

Thr Tyr  Gln Asn Lys Val Val  Arg Val Gln Arg Pro  Ala Lys Asn
    3065                 3070                 3075

Gly Thr  Val Met Asp Val Ile  Ser Arg Arg Asp Gln  Arg Gly Ser
    3080                 3085                 3090

Gly Gln  Val Gly Thr Tyr Gly  Leu Asn Thr Phe Thr  Asn Met Glu
    3095                 3100                 3105

Ala Gln  Leu Ile Arg Gln Met  Glu Ser Glu Gly Ile  Phe Leu Pro
    3110                 3115                 3120

Ser Glu  Leu Glu Thr Pro Asn  Leu Ala Gly Arg Val  Leu Asp Trp
    3125                 3130                 3135

Leu Glu  Lys Tyr Gly Val Glu  Arg Leu Lys Arg Met  Ala Ile Ser
    3140                 3145                 3150

Gly Asp  Asp Cys Val Val Lys  Pro Ile Asp Asp Arg  Phe Ala Thr
    3155                 3160                 3165

Ala Leu  Thr Ala Leu Asn Asp  Met Gly Lys Val Arg  Lys Asp Ile
    3170                 3175                 3180

Pro Gln  Trp Glu Pro Ser Lys  Gly Trp Asn Asp Trp  Gln Gln Val
```

-continued 3185 3190 3195

Pro Phe Cys Ser His His Phe His Gln Leu Ile Met Lys Asp Gly
3200 3205 3210

Arg Glu Ile Val Val Pro Cys Arg Asn Gln Asp Glu Leu Val Gly
3215 3220 3225

Arg Ala Arg Val Ser Gln Gly Ala Gly Trp Ser Leu Arg Glu Thr
3230 3235 3240

Ala Cys Leu Gly Lys Ser Tyr Ala Gln Met Trp Gln Leu Met Tyr
3245 3250 3255

Phe His Arg Arg Asp Leu Arg Leu Ala Ala Asn Ala Ile Cys Ser
3260 3265 3270

Ala Val Pro Val Asp Trp Val Pro Thr Ser Arg Thr Thr Trp Ser
3275 3280 3285

Ile His Ala His His Gln Trp Met Thr Thr Glu Asp Met Leu Ser
3290 3295 3300

Val Trp Asn Arg Val Trp Ile Glu Glu Asn Pro Trp Met Glu Asp
3305 3310 3315

Lys Thr His Val Ser Ser Trp Glu Glu Val Pro Tyr Leu Gly Lys
3320 3325 3330

Arg Glu Asp Gln Trp Cys Gly Ser Leu Ile Gly Leu Thr Ala Arg
3335 3340 3345

Ala Thr Trp Ala Thr Asn Ile Gln Val Ala Ile Asn Gln Val Arg
3350 3355 3360

Arg Leu Ile Gly Asn Glu Asn Tyr Leu Asp Tyr Met Thr Ser Met
3365 3370 3375

Lys Arg Phe Lys Asn Glu Ser Asp Pro Glu Gly Ala Leu Trp
3380 3385 3390

<210> SEQ ID NO 42
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: LAV2

<400> SEQUENCE: 42
agttgttagt ctacgtggac cgacaaagac agattctttg agggagctaa gctcaatgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggttggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acacgaactg aaacatggat gtcatcagaa 780

-continued

```
ggggcctgga aacatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccctttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
```

-continued

```
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgw gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
```

-continued gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattctt gatgagcgca 6600 aggggcatag ggaagatgac cctgggaatg tgctgcataa tcacggctag catcctccta 6660
tggtacgcac aaatacagcc acactggata gcagcttcaa taatactgga gtttttctc 6720 atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa catagggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920

-continued acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460
cacccataca aaacgtgggc ataccatggt agctatgaaa caaaacagac tggatcagca 8520
tcatccatgg tcaacggagt ggtcaggctg ctgacaaaac cttgggacgt tgtccccatg 8580
gtgacacaga tggcaatgac agacacgact ccatttggac aacagcgcgt tttaaagag 8640
aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccatattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260

-continued gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 43
<211> LENGTH: 10699
<212> TYPE: DNA
<213> ORGANISM: Dengue virus
<220> FEATURE:
<221> NAME/KEY: misc_feature
<222> LOCATION: (1)..(10699)
<223> OTHER INFORMATION: LAV3

<400> SEQUENCE: 43
agttgttagt ctacgtggac cgacaagaac agtttcgact cggaagcttg cttaacgtag 60
tgctgacagt tttttattag agagcagatc tctgatgaac aaccaacgga aaaagacggg 120
aaaaccgtct atcaatatgc tgaaacgcgt gagaaaccgt gtgtcaactg gatcacagtt 180
ggcgaagaga ttctcaagag gattgctgaa cggccaagga ccaatgaaat tggttatggc 240
atttatagct ttcctcagat ttctagccat tccaccgaca gcaggagtct tggctagatg 300
gggtaccttt aagaagtcgg gggctattaa ggtcttaaaa ggcttcaaga aggagatctc 360
aaacatgctg agcattatca acaaacggaa aaagacatcg ctctgtctca tgatgatgtt 420
accagcaaca cttgctttcc acttaacttc acgagatgga gagccgcgca tgattgtggg 480
gaagaatgaa agaggaaaat ccctactttt caagacagcc tctggaatca acatgtgcac 540
actcatagct atggatctgg gagagatgtg tgatgacacg gtcacttaca aatgccccca 600
cattaccgaa gtggagcctg aagacattga ctgctggtgc aaccttacat cgacatgggt 660
gacttatgga acatgcaatc aagctggaga gcatagacgc gataagagat cagtggcgtt 720
agctccccat gttggcatgg gactggacac acgcactcaa acctggatgt cggctgaagg 780
agcttggaga caagtcgaga aggtagagac atgggccctt aggcacccag ggtttaccat 840
actagcccta tttcttgccc attacatagg cacttccttg acccagaaag tggttatttt 900
tatactatta atgctggtta ccccatccat gacaatgaga tgtgtaggag taggaaacag 960
agattttgtg gaaggcctat cgggagctac gtgggttgac gtggtgctcg agcacggtgg 1020
gtgtgtgact accatggcta agaacaagcc cacgctggac atagagcttc agaagaccga 1080
ggccacccaa ctggcgaccc taaggaagct atgcattgag ggaaaaatta ccaacataac 1140
aaccgactca agatgtccca cccaagggga agcgatttta cctgaggagc aggaccagaa 1200
ctacgtgtgt aagcatacat acgtggacag aggctgggga aacggttgtg gtttgtttgg 1260
caagggaagc ttggtgacat gcgcgaaatt tcaatgttta gaatcaatag agggaaaagt 1320
ggtgcaacat gagaacctca aatacaccgt catcatcaca gtgcacacag gagaccaaca 1380
ccaggtggga aatgaaacgc agggagtcac ggctgagata acaccccagg catcaaccgc 1440
tgaagccatt ttacctgaat atggaaccct cgggctagaa tgctcaccac ggacaggttt 1500
ggatttcaat gaaatgatct yattgacaat gaagaacaaa gcatggatgg tacatagaca 1560

-continued

```
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaagggatga gctatgcaat gtgcttgggt agctttgtgt tgaagaaaga   1860
agtctccgaa acgcagcatg ggacaatact cattaaggtt gagtacaaag ggaaagatgc   1920
accctgcaag attcctttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggct actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
ctcctggatg atgaaaattg gaataggtgt cctcttaacc tggatagggt tgaactcaaa   2340
aaatacttct atgtcatttt catgcatcgc gataggaatc attacactct atctgggagc   2400
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
cgacatgggc tattggatag aaagccaaaa gaatgggagt tggaagctag aaaaagcatc   3060
cttcatagag gtgaaaacct gcacatggcc aaaatcacac actctctgga gcaatggtgt   3120
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa aactgtggga caagaggccc   3300
atcattgaga acaacaacgg tgtcagggaa gttgatacac gaatggtgct gccgctcgtg   3360
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccactcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttggggc tcatggctct taaactgata acacaatttg aaacatacca   3900
```

-continued

```
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080
accacttttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatggaa caatgagaat   4380
aaaagatgac gagactgaga acatcttaac agtgctttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaaggggtct ataggatcaa acagcaagga atttttggga aaacccaagt   4620
gggggttgga gtacagaaag aaggagtttt ccacaccatg tggcatgtca caagaggggc   4680
agtgttgaca cacaatggga aaagactgga accaaactgg gctagcgtga aaaaagatct   4740
gatttcatac ggaggaggat ggagattgag tgcacaatgg aaaaaggggg aggaggtgca   4800
ggttattgcc gtagagcctg ggaagaaccc aaagaacttt caaaccatgc caggcatttt   4860
tcagacaaca acaggggaaa taggagcaat tgcactggat ttcaagcctg gaacttcagg   4920
atctcccatc ataaacagag agggaaaggt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaacaccc cctggaacag ctgatgcctt tcctcagagc aacgctccaa ttcaagatga   5520
agagagagac ataccggaac gctcatggaa ttcaggcaat gaatggatta ctgactttgt   5580
tgggaagaca gtgtggtttg tccctagcat caaagccgga aatgacatag caaactgctt   5640
gcggaaaaat ggaaaaaagg ttattcaact cagcaggaag acctttgaca cagaatatca   5700
aaagaccaaa ctgaatgatt gggactttgt ggtgacaaca gacatttcag aaatgggagc   5760
caatttcaaa gcagatagag tgatcgaccc aagaagatgt ctcaagccgg tgattttgac   5820
agatggaccc gagcgggtga tcctggctgg accaatgcca gtcaccgtag cgagcgctgc   5880
gcaaaggaga gggagagttg gcaggaaccc acaaaaagaa aatgaccagt acatattcat   5940
gggccagcct ctcaacaatg atgaagacca tgctcactgg acagaagcaa aaatgctgct   6000
ggacaacatc aacacaccag aagggattat accagctctc tttgaaccag aaagggagaa   6060
gtcagccgcc atagacggcg aataccgcct gaagggtgag tccaggaaga ctttcgtgga   6120
actcatgagg aggggtgacc tcccagtttg gctagcccat aaagtagcat cagaagggat   6180
caaatataca gatagaaaat ggtgctttga tggagaacgt aataatcaaa ttttagagga   6240
gaatatggat gtggaaatct ggacaaagga aggagaaaag aaaaaactga gacctaggtg   6300
```

-continued

```
gcttgatgcc cgcacttatt cagatccttt agcactcaaa gaattcaagg attttgcagc   6360
tggcagaaag tcaatcgccc ttgatcttgt gacagaaata ggaagagtgc cttcacactt   6420
agcccacaga acgagaaacg ccctggataa tttggtgatg ctgcacacgt cagaacatgg   6480
cggtagggcc tacaggcatg cagtggagga actaccagaa acgatggaaa cactcttact   6540
cctgggactg atgatcttgt taacaggtgg agcaatgctc ttcttgatat caggtaaagg   6600
gattggaaag acttcaatag gactcatttg tgtaattgct tccagcggca tgttatggat   6660
ggctgatgtc ccactccaat ggatcgcatc ggctatagtc ctggagtttt ttatgatggt   6720
gttgctcata ccagaaccag aaaagcagag aactccccaa gacaaccaac tcgcatatgt   6780
cgtgataggc atacttacat tggctgcaat agtagcggcc aatgaaatgg gactgttgga   6840
aactacaaag agagatttag gaatgtctaa agaaccaggt gttgtttctc caaccagcta   6900
tttggatgtg gacttgcacc cagcatcagc ctggacattg tacgccgtgg ccacaacagt   6960
aataacacca atgttgagac acaccataga gaattccaca gcaaatgtgt ctctggcagc   7020
catagctaac caggcagtgg tcctgatggg tttagacaaa ggatggccga tatcgaaaat   7080
ggacttgggc gtaccactat tggcactggg ttgctattca caagtgaacc cactaactct   7140
tgcagcggca gtacttttgc tagtcacaca ttatgcaatt ataggtccag gattgcaggc   7200
aaaagccacc cgtgaagctc agaaaaggac agctgctgga ataatgaaga atccaacggt   7260
ggatggaata atgacaatag acctagatcc tgtaatatat gattcaaaat ttgaaaagca   7320
actaggacag gtcatgctcc tggttctgtg tgcagtccaa cttttattga tgagaacatc   7380
atgggccttg tgtgaagttc taaccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg gaacaggaaa   7560
gagaggaaca gggtcacaag gtgaaacctt aggagaaaag tggaaaaaga aattaaatca   7620
gttatcccgg aaagagtttg acctttacaa gaaatccgga atcaccgaag tggatagaac   7680
agaagccaaa gaagggttaa aaagaggaga aataacacac catgccgtgt ccagaggcag   7740
cgcaaaactt caatggttcg tggagagaaa catggtcatt cctgaaggaa gagtcataga   7800
cctaggctgt ggaagaggag gctggtcata ttactgtgca ggactgaaaa aagttacaga   7860
agtgcgagga tacacaaaag gcggcccagg acacgaagaa ccagtaccta tgtctacata   7920
cggatggaac atagtcaagt taatgagtgg aaaggatgtt ttttatctgc cacctgaaaa   7980
gtgtgatacc ctattgtgtg acattggaga atcttcacca agcccaacag tggaagaaag   8040
cagaaccata agagttttga agatggttga accatggcta aagaacaacc agttttgcat   8100
taaagtattg aacccataca tgccaactgt gattgagcac ttagaaagac tacaaaggaa   8160
acatggagga atgcttgtga gaaatccact ctcacgaaac tccacgcacg aaatgtattg   8220
gatatccaat ggtacaggca atatcgtctc ttcagtcaac atggtatcca gattgctact   8280
gaacagattc acaatgacac acaggagacc caccatagag aaagatgtgg atctaggagc   8340
aggaacccga catgtcaatg cggaaccaga aacacccaac atggatgtca ttggggaaag   8400
aataaaaagg atcaaagagg agcatagttc aacatggcac tatgatgatg aaaatcctta   8460
caaaacgtgg gcttaccatg gatcctatga agtaaaagcc acaggctcag cctcctccat   8520
gataaatgga gtcgtgaaac tcctcacaaa accatgggat gtggtgccca tggtgacaca   8580
gatggcaatg acagatacaa ctccattcgg ccagcaaaga gtttttaaag agaaagtgga   8640
```

-continued

```
caccaggaca cctaggccca tgccaggaac aagaaaggtt atggagatca cagcggagtg   8700

gctttggagg accctgggaa ggaacaaaag acccagatta tgcacaaggg aggaattcac   8760

aaagaaggtc agaaccaacg cagctatggg cgctgtcttc acagaagaga accaatggga   8820

cagtgcgaga gctgctgttg aggacgaaga attttggaaa cttgtggaca gagaacgtga   8880

actccacaaa ctgggcaagt gtggaagctg cgtttacaac atgatgggca agagagagaa   8940

aaaacttgga gagtttggta aagcaaaagg cagtagggct atatggtaca tgtggttggg   9000

agccaggtac cttgagttcg aggcgctcgg attcctcaat gaagaccact ggttctcgcg   9060

tgaaaactct tacagtggag tagaaggaga aggactgcac aagctgggat acatcttgag   9120

agatatttcc aagatacccg gaggagccat gtatgctgat gacacagccg gttgggacac   9180

aagaataaca gaagatgacc tgcacaatga ggaaaaaatc acacagcaga tggaccctga   9240

acacaggcag ctagcgaacg ctatattcaa gctcacatac caaaacaaag tggtcaaagt   9300

ccaacgacca actccaaagg gcacggtaat ggacatcata tctaggaaag accaaagagg   9360

cagtggacag gtgggaactt atggtctgaa cacattcacc aacatggaag cccagctaat   9420

cagacaaatg gaaggagaag gcgtgttgtc aaaggcagac ctcgagaacc cccatccgct   9480

agagaagaaa attacacaat ggttggaaac taaaggagtg gaaaggttaa aaagaatggc   9540

catcagcggg gatgattgcg ttgtgaaacc aatcgacgac agattcgcca atgccctgct   9600

tgccctgaac gatatgggaa aggttagaaa ggacatacct caatggcagc catcaaaggg   9660

atggcatgat tggcaacagg tccccttctg ctcccaccac tttcatgaat tgatcatgaa   9720

agatggaaga aagttggtag ttccctgcag accccaggac gaactaatag gaagagcgag   9780

aatctcccaa ggagcaggat ggagccttag agaaactgca tgtctaggga aagcctacgc   9840

tcaaatgtgg gctctcatgt attttcacag aagagatctt agactagcat ccaacgccat   9900

atgttcagca gtaccagtcc actgggtccc cacgagcaga acgacatggt ctattcatgc   9960

tcaccatcag tggatgacta cagaagacat gcttactgtc tggaacaggg tgtggataga  10020

ggacaatcca tggatggaag acaaaactcc agtcacaacg tgggaagatg ttccatatct  10080

agggaagaga gaagaccaat ggtgcggatc actcataggt ctcacttcca gagcaacctg  10140

ggcccagaac atactcacag caatccaaca ggtgagaagc ctcataggca atgaagagtt  10200

tctggactac atgccttcga tgaagagatt caggaaggag gaggagtcag agggagccat  10260

ttggtaaaag caggaggtaa actgtcaggc cacattaagc cacagtacgg aagaagctgt  10320

gcagcctgtg agccccgtcc aaggacgtta aaagaagaag tcaggcccaa aagccacggt  10380

ttgagcaaac cgtgctgcct gtagctccgt cgtggggacg taaagcctgg gaggctgcaa  10440

accgtggaag ctgtacgcac ggtgtagcag actagtggtt agaggagacc cctcccatga  10500

cacaacgcag cagcggggcc cgagcactga gggaagctgt acctccttgc aaaggactag  10560

aggttagagg agaccccccg caaacaaaaa cagcatattg acgctgggag agaccagaga  10620

tcctgctgtc tcctcagcat cattccaggc acagaacgcc agaaaatgga atggtgctgt  10680

tgaatcaaca ggttctagt                                                10699
```

<210> SEQ ID NO 44
<211> LENGTH: 10648
<212> TYPE: DNA
<213> ORGANISM: Dengue virus
<220> FEATURE:
<221> NAME/KEY: misc_feature
<222> LOCATION: (1)..(10648)
<223> OTHER INFORMATION: LAV4

-continued

<400> SEQUENCE: 44

```
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggaccctta cggatggtgc    240
tagcattcat cacgtttttg cgagtccttt ccatccccacc aacagcaggg attctgaaaa    300
gatggggaca gttgaagaaa aataaggcca tcaggatact gattggattc aggaaggaga    360
taggccgcat gctgaacatc ttgaacggga gaaaaaggtc aacgataaca ttgctgtgct    420
tgattcccac cgtaatggcg tttcacttgt caacaagaga tggcgaaccc ctcatgatag    480
tggcaaaaca tgaaaggggg agacctctct tgtttaagac aacagagggg atcaacaaat    540
gcactctcat tgccatggac ttgggtgaaa tgtgtgagga cactgtcacg tataaatgcc    600
ccttactggt caataccgaa cctgaagaca ttgattgctg gtgcaatctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgccccat cctacggaat gcgatgcgta ggagtaggaa    960
acagagactt tgtggaagga gtctcaggtg gagcatgggt cgatctggtg ctagaacatg   1020
gaggatgcgt cacaaccatg gcccagggaa aaccaacctt ggattttgaa ctgactaaga   1080
caacagccaa ggaagtggct ctgttaagaa cctattgcat tgaagcctca atatcaaaca   1140
taaccacggc aacaagatgt ccaacgcaag gagagcctta tctaaaagag gaacaagacc   1200
aacagtacat ctgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccacgata actcccaggt   1440
caccatcggt ggaagtcaaa ttgccggact atggagaact aacactcgat tgtgaaccca   1500
ggtctggaat tgactttaat gagatgattc tgatgaaaat gaaaaagaaa acatggcttg   1560
tgcataagca atggtttttg gatctacctc taccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatctcaag tgcaaagtcc   1800
gtatggagaa attgagaatc aagggaatgt catacacgat gtgttcagga aagttctcaa   1860
ttgacaaaga gatggcagaa acacagcatg ggacaacagt ggtgaaagtc aagtatgaag   1920
gtgctggagc tccgtgtaaa gtccccatag agataagaga tgtgaacaag aaaaaagtgg   1980
ttgggcgtat catctcatcc acccctttgg ctgagaatac caacagtgca accaacatag   2040
agttagaacc cccctttggg gacagctaca tagtgatagg tgttggaaac agtgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggtttttgg aagtgtgtat acaaccatgt   2280
```

-continued

```
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
gggtctgtgg aattagatca accacgaggc tggaaaatgt catgtggaag caaataacca   2640
acgagctaaa ttatgttctc tgggaaggag gacatgacct cactgtagtg gctggggatg   2700
tgaagggggt gttgaccaaa ggcaagagag cactcacacc cccagtgaat gatctgaaat   2760
attcatggaa gacatgggga aaagcaaaaa tcttcacccc agaagcaaga aatagcacat   2820
ttttaataga cggaccagac acctccgaat gccccaatga acgaagagca tggaactttc   2880
ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acattgtgga   3120
gcaatggagt gctggaaagc cagatgctca ttccaaaatc atatgcgggc cctttttcac   3180
accacaatta ccgccagggc tatgccacgc aaaccgtggg cccatggcac ttaggcaaat   3240
tagagataga ctttggagaa tgccccggaa caacagtcgc aattcaggag gattgtgacc   3300
atagaggccc atctttgagg accaccactg catctggaaa actagtcacg caatggtgct   3360
gccgctcctg cacgatgcct cccttaaggt tcttgggaga agatgggtgc tggtatggga   3420
tggagattag gcccttgagt gaaaaagaag agaacatggt caaatcacag gtaacggccg   3480
gacagggcac atcagaaact tttctatgg gtctgttgtg cctgaccttg tttgtggaag   3540
aatgcttgag gagaagagtc actaggaaac acatgatatt ggttgtggtg atcactcttt   3600
gtgccatcat cctaggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctggggctaa ttttgctaaa aatagtgaca cattttgaca   3900
acacccaagt gggaacctta gccctttcct tgaccttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt ccctttagct ggcccaatgg tggcaggagg cttacttctg gcggcttacg   4260
tgatgagtgg tagctcagca gatctgtcac tagagaaggc cgccaatgtg cagtgggatg   4320
aaatggcaga cataacaggc tcaagcccaa tcatagaagt gaagcaggat gaagatggct   4380
ctttctccat acgggacgtc gaggaaacca atatgataac ccttttggtg aaactggcac   4440
tgataacagt gtcaggtctc taccccttgg caattccagt cacaatgacc ttatggtaca   4500
tgtggcaagt gaaaacacaa agatcaggag ccctgtggga cgtcccctca cccgctgcca   4560
ctcaaaaagc cgcactgtct gaaggagtgt acaggatcat gcaaagaggg ttatttggga   4620
aaactcaggt tggagtaggg atacacatgg aaggtgtatt tcacacaatg tggcatgtaa   4680
```

-continued caagaggatc agtgatctgc catgagactg ggagattgga gccatcttgg gctgacgtca 4740
ggaatgacat gatatcatac ggtgggggat ggagacttgg agacaaatgg gacaaagaag 4800
aagatgttca ggtcctcgcc atagaaccag gaaaaaatcc taaacatgtc caaacgaaac 4860
ccggcctttt caagacccta actggagaaa ttggagcagt aacattagat ttcaaacccg 4920
gaacgtctgg ttctcccatc atcaacagga aaggaaaagt catcggactc tatggaaatg 4980
gagtagttac caaatcaggt gattacgtca gtgccataac gcaagccgaa agaattggag 5040
agccagatta tgaagtggat gaggacattt ttcgaaagaa aagattaact ataatggact 5100
tacaccccgg agctggaaag acaaaaagaa ttcttccatc aatagtgaga gaagccttaa 5160
aaaggaggct gcgaaccttg attttggctc ccacgagagt ggtggcggcc gagatggaag 5220
aggccctacg tggactgcca atccgttatc agaccccagc tgtgaaatca gaacacacag 5280
gaagagagat tgtagacctc atgtgtcatg caaccttcac aacaagactt ttgtcatcaa 5340
ccagagttcc aaattacaac ctcatagtga tggatgaagc acatttcacc gatccttcta 5400
gtgtcgcggc tagaggatac atctcgacca gggtggaaat gggagaggca gcagccatct 5460
tcatgaccgc aacccctccc ggagcgacag atccctttcc ccagagcaac agcccaatag 5520
aagacatcga gagggaaatt ccggaaaggt catggaacac agggttcgac tggataacag 5580
actaccaagg gaaaactgtg tggtttgttc ccagcataaa agctggaaat gacattgcaa 5640
attgtttgag aaagtcggga aagaaagtta tccagttgag taggaaaacc tttgatacag 5700
agtatccaaa aacgaaactc acggactggg attttgtggt cactacagac atatctgaaa 5760
tgggggccaa ttttagagct gggagagtga tagaccctag gagatgcctc aagccagtta 5820
tcctaacaga tgggccagag agagtcattt tagcaggtcc tattccagtg actccagcaa 5880
gcgctgctca gagaagaggg cgaataggaa ggaacccagc acaagaagac gaccaatacg 5940
ttttctccgg agacccacta aaaaatgatg aagatcatgc ccactggaca gaagcaaaga 6000
tgctgcttga caatatctac accccagaag ggatcattcc aacattgttt ggtccggaaa 6060
gggaaaaaac ccaagccatt gatggagagt ttcgcctcag aggggaacaa aggaagactt 6120
ttgtggaatt aatgaggaga ggagaccttc cggtgtggct gagctataag gtagcttctg 6180
ctggcatttc ttacaaagat cgggaatggt gcttcacagg ggaaaggaat aaccaaattt 6240
tagaagaaaa catggaggtt gaaatttgga ctagagaggg agaaaagaaa aagctaaggc 6300
caagatggtt agatgcacgt gtatacgctg accccatggc tttgaaggat tttaaggagt 6360
ttgctagtgg aaggaagagc ataactctcg acatcctaac agagattgcc agtttgccaa 6420
cttacctttc ctctagggcc aagctcgccc ttgataacat agtcatgctc cacacaacag 6480
aaagaggagg gagggcctac caacacgccc tgaacgaact cccggagtca ctggaaacac 6540
ttatgcttgt agctttacta ggtgctatga cagcaggtat cttcctgttt ttcatgcaag 6600
ggaaaggaat agggaaattg tcaatgggtt tgataaccat tgcggtggct agtggcttgt 6660
tctgggtagc agaaattcaa ccccagtgga tagcggcctc aatcatacta gagtttttc 6720
tcatggtact gttgataccg gaaccagaaa aacaaaggac cccacaagac aatcaattga 6780
tctacgtcat attgaccatt ctcaccatta ttggtctcat agcagccaac gagatggggc 6840
tgattgaaaa aacaaaaacg gattttgggt tttaccaggt aaaaacagaa accaccatcc 6900
tcgatgtgga cttgagacca gcttcagcat ggacgctcta tgcagtagcc accacawttc 6960
tgactcccat gctgagacac accatagaaa acacgtcggc caacctatct ctagcagcca 7020

-continued

```
ttgccaacca ggcggccgtc ctaatggggc ttggaaaagg atggccgctc cacagaatgg   7080
acctcggtgt gccgctgtta gcaatgggat gctattctca agtgaaccca acaactttga   7140
cagcatcctt agtcatgctt tcagtccatt atgcaataat aggtccagga ttgcaggcaa   7200
aagccacaag agaggcccag aaaaggacag ctgctgggat catgaaaaac cccacggtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcaggggaa   7500
gttacctggc gggagctgga ctggcttttt cactcataaa gaatgyacaa acccctagga   7560
ggggaactgg gaccacagga gagacactgg gagagaagtg gaagagacag ctaaactcat   7620
takacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga aacattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg ggcgtatcat ggaagctatg aagctccttc gacaggctct gcatcctcca   8520
tggtgaacgg ggtagtaaaa ctgctaacaa aaccttggga tgtggttcca atggtgaccc   8580
agttagccat gacagacaca accccttttg ggcaacaaag agtgttcaaa gagaaggtgg   8640
ataccagaac accacaacca aaacccggta cacgaatggt tatgaccacg acagccaatt   8700
ggctgtgggc cctccttggg aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctacaa catgatggga aaacgtgaga   8940
aaaagttagg agagtttggc agagccaagg gaagccgagc aatctggtac atgtggctgg   9000
gagcgcggtt tctggaattt gaagccctgg gtttttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aagaactgat cacggaacag atggcccccc   9240
accacaagat cctagccaaa gccattttca aactaaccta tcaaaacaaa gtggtgaaag   9300
tcctcagacc cacaccgaga ggagcggtga tggatatcat atccaggaaa gaccaaagag   9360
gtagtggaca agttggaaca tatggtttga acacattcac caacatggaa gttcaactca   9420
```

-continued

```
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctggatga gaggtttggc acttccctcc    9600
tcttcttgaa cgacatggga aaggtgagga aagacattcc gcagtgggaa ccatctaagg    9660
gatggaaaaa ctggcaagag gttccttttt gctcccacca ctttcacaag atcttcatga    9720
aggatggccg ctcactagtt gttccatgta gaaaccagga tgaactgata gggagagcca    9780
gaatctcgca gggggctgga tggagcttaa gagaaacagc ctgcctgggc aaagcttacg    9840
cccagatgtg gtcgctcatg tacttccaca gaagggatct gcgtttagcc tccatggcca    9900
tatgctcagc agttccaacg gaatggtttc caacaagcag aacaacatgg tcaatccacg    9960
ctcatcatca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcacacg gccataaccc aggtcagaaa cctgatcgga aaagaggaat   10200
acgtggatta catgccagta atgaaaagat acagcgctcc ttcagagagt gaaggagttc   10260
tgtaattacc aacaacaaac accaaaggct attgaagtca ggccacttgt gccacggctt   10320
gagcaaaccg tgctgcctgt agctccgcca ataatgggag gcgtgaaatc cctagggagg   10380
ccatgcgcca cggaagctgt acgcgtggca tattggacta gcggttagag gagacccctc   10440
ccatcactga caaaacgcag caaaaggggg cccgaagcca ggaggaagct gtactcctgg   10500
tggaaggact agaggttaga ggagaccccc ccaacacaaa aacagcatat tgacgctggg   10560
aaagaccaga gatcctgctg tctctgcaac atcaatccag gcacagagcg aagcaagatg   10620
gattggtgtt gttgatccaa caggttct                                      10648
```

DENGUE SEROTYPE 1 ATTENUATED STRAIN

CROSS-REFERENCE TO RELATED APPLICATIONS

The present application claims the benefit of U.S. provisional application 60/691,243, filed on Jun. 17, 2005, incorporated herein by reference.

The invention relates to new live attenuated VDV1 (VERO-Derived Dengue serotype 1 virus) strains which are derived from the wild-type dengue-1 strain 16007 by passaging on PDK and Vero cells, and sanitization. The invention further relates to a vaccine composition which comprises such VDV1 strain.

Dengue diseases are caused by four closely related, but antigenically distinct, virus serologic types (Gubler, 1988; Kautner et al., 1997; Rigau-Pérez et al., 1998; Vaughn et al., 1997), of the genus *Flavivirus* (Gubler, 1988). Infection with a dengue virus serotype can produce a spectrum of clinical illnesses ranging from a non-specific viral syndrome to severe, fatal haemorrhagic disease. The incubation period of dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Pérez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

Dengue haemorrhagic fever (DHF) is a severe febrile disease characterised by abnormalities of homeostasis and increased vascular permeability that can lead to hypovolemia and hypotension (dengue shock syndrome, DSS) often complicated by severe internal bleeding. The case fatality rate of DHF can be as high as 10% without therapy, but below 1% in most centres with therapeutic experience (WHO Technical Guide, 1986).

Routine laboratory diagnosis of dengue infections are based on virus isolation and/or the detection of dengue virus-specific antibodies.

Dengue disease is the second most important tropical infectious disease after malaria, with over half of the world's population (2.5 billion) living in areas at risk for epidemic transmission. An estimated 50 to 100 million cases of dengue, 500,000 hospitalized DHF patients and 25,000 deaths occur each year. Dengue is endemic in Asia, the Pacific, Africa, Latin America, and the Caribbean. More than 100 tropical countries have endemic dengue virus infections, and DHF have been documented in more than 60 of these (Gubler, 2002; Monath, 1994). A number of well described factors appear to be involved in dengue infections: population growth, unplanned and uncontrolled urbanization particularly in association with poverty, increased air travel, lack of effective mosquito control, and the deterioration of sanitary and public health infrastructure (Gubler, 2002). The awareness of dengue in travelers and expatriates is increasing (Shirtcliffe et al., 1998). Dengue has proven to be a major cause of febrile illness among US troops during deployments in dengue-endemic tropical areas (DeFraites et al., 1994).

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases, including some viruses belonging to the same genus as dengue (examples of commercially available flavivirus live-attenuated vaccines include yellow fever and Japanese encephalitis vaccines). The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotype 1 (strain 16007, passage 13=LAV1), serotype 2 (strain 16681, passage 53), and serotype 4 (strain 1036, passage 48) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3). These vaccines have been tested as monovalent (single serotype), bivalent (two serotypes), trivalent (three serotypes), and tetravalent (all four serotypes) vaccines in Thai volunteers. Those vaccines were found to be safe and immunogenic in children and in adults (Gubler, 1997). These LAV 1-4 strains have been described in EP 1159968 in the name of the Mahidol University and were deposited before the CNCM (CNCM I-2480; CNCM I-2481; CNCM I-2482 and CNCM I-2483 respectively).

The complete sequence of the Dengue 1 Live-Attenuated Virus strain (LAV1) was established by R. Kinney et al. (CDC, Fort Collins). Sequence differences between parent DEN-1 strain 16007 (SEQ ID No.2) and LAV1 (SEQ ID No.3) strain are described in Table 1. Thus, genetic comparison of the wild-type virus strain 16007 and LAV1 strain showed a set of 14 point mutations which could be linked to LAV1 attenuation.

TABLE 1

DEN-1 16007 and DEN-1 16007/PDK13 (LAV1) Sequence Differences

| Coordinates | | LAV1 (DEN-1 16007/ PDK13) | | 16007 | |
|---|---|---|---|---|---|
| Gene-aa | position | Nt | aa | nt | aa |
| **E-130** | **Nt-1323** | **C** | **Ala** | **T** | **Val** |
| **E-203** | **Nt-1541** | **A** | **Lys** | **G** | **Glu** |
| | **Nt-1543** | **G** | | **A** | |
| **E-204** | **Nt-1545** | **A** | **Lys** | **G** | **Arg** |
| E-211 | Nt-1567 | G | Gln | A | Gln |
| **E-225** | **Nt-1608** | **T** | **Leu** | **C** | **Ser** |
| **E-477** | **Nt-2363** | **G** | **Val** | **A** | **Met** |
| NS1-92 | Nt-2695 | C | Asp | T | Asp |
| NS1-121 | Nt-2782 | T | Ala | C | Ala |
| **NS3-182** | **Nt-5063** | **A** | **Lys** | **G** | **Glu** |
| **NS3-510** | **Nt-6048** | **T** | **Phe** | **A** | **Tyr** |
| **NS4A-144** | **Nt-6806** | **G** | **Val** | **A** | **Met** |
| NS4B-168 | Nt-7330 | G | Gln | A | Gln |
| NS5-624 | Nt-9445 | T | Ser | C | Ser |

Nucleotide changes modifying the corresponding codon are indicated in bold.

The LAV1 strain which was initially established in 1983 was further rapidly identified as potential vaccine candidate (Bhamarapravati and Yoksan, 1997).

However, at that time, transmission to humans of Spongiform Encephalitis through mammalian cultures was not perceived as a risk and the virus was routinely maintained in Primary Dog Kidney cells (PDK). Furthermore, this LAV1 strain corresponds to a heterogeneous population. This heterogeneity represents an additional risk due to a potential in vitro or in vivo selection of one of the strain present in the composition.

In view of these increasing concerns, the Applicant decided to set up a sanitization process in order to get rid of any such risks. By first transferring the LAV1 vaccine strain from PDK to VERO cells and then transfecting Vero cells with the purified genomic RNA of LAV1, followed by two successive steps of virus plaque purification the Applicant produced a new Vero-Derived serotype 1 virus (VDV1).

This new VDV1 strain which has been thus derived by transfer to VERO cells and biological cloning differs from the LAV1 strain by sequence, an homogenous plaque size and temperature sensitivity but importantly has conserved some phenotypic and genotypic features of the LAV1 such as e.g. attenuation spots, small plaque phenotype, growth restriction at high temperature, and has conserved the immunogenic features of the LAV1 strains. These features make this new strain a valuable vaccine candidate for prophylactic immunization in humans.

DEFINITIONS

"Dengue viruses" are positive-sense, single-stranded RNA viruses belonging to the *Flavivirus* genus of the Flaviviridae family. In the case of dengue serotype 1 (DEN-1) strain 16007, the entire sequence is 10735 nucleotides long (SEQ ID No.2). The RNA genome contains a type I cap at the 5'-end but lacks a 3'-end poly (A)-tail. The gene organization is 5'-noncoding region (NCR), structural protein (capsid (C), premembrane/membrane (prM/M), envelope (E)) and non structural protein (NS1-NS2A-NS2B-NS3-NS4A-NS4B-NS5) and 3'NCR. The viral RNA genome is associated with the C proteins to form nucleocapsid (icosahedral symmetry). As with other flaviviruses, the DEN viral genome encodes the uninterrupted open reading frame (ORF) which is translated to a single polyprotein.

Serial passaging of a virulent (disease-causing) strain of dengue-1 results in the isolation of modified virus which are "live attenuated", i.e., infectious, yet not capable of causing disease. These modified viruses are usually tested in monkeys to evaluate their attenuation. However, Humans are the only primates that exhibit signs of clinical disease. The viruses that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response are called "live attenuated".

The term "LAV" denotes live attenuated Dengue viral strains. In the context of the invention "LAVs" are live attenuated strains initially derived from the Dengue serotype 1 (DEN-1) strain 16007 by passages, e.g. 10, 11, 12 or 13 passages, in Primary Dog Kidney (PDK) Cells. For instance "LAV1/PDK13" is the attenuated strain established after 13 passages of strain 16007 in PDK cells (also named DEN-1 16007/PDK13). LAV1/PDK13 nucleotide sequence is shown in SEQ ID No.3.

"VDV1" is meant a LAV obtainable by the sanitization process disclosed in the present application. A VDV1 is thus a biological clone (homogeneous) VERO-adapted Dengue serotype 1 virus capable of inducing a specific humoral immune response including neutralizing antibodies in primate especially in humans. The VDV1 strains of the invention can be easily reconstructed starting directly from the here disclosed VDV1 sequences. The induction of a specific humoral immune response can be easily determined by an ELISA assay. The presence of neutralizing antibody in the serum of a vaccinee is evaluated by the plaque reduction neutralization test as described in section 4.1.2.2. A serum is considered to be positive for the presence of neutralizing antibodies when the neutralizing antibody titer thus determined is at least superior or equal to 1:10.

The terms "mutation" means any detectable change in genetic material, e.g. DNA, RNA, cDNA, or any process, mechanism, or result of such a change. Mutations include substitutions of one or more nucleotides. In the context of the instant application, mutations identified in dengue-1 virus genomic sequence or polyprotein are designated pursuant to the nomenclature of Dunnen and Antonarakis (2000). As defined by Dunnen and Antonarakis at the nucleic acid level, substitutions are designated by ">", e.g. "31A>G" denotes that at nucleotide 31 of the reference sequence a A is changed to a G.

Variations at the protein level describe the consequence of the mutation and are reported as follows. Stop codons are designated by X (e.g. R97X denotes a change of Arg96 to a termination codon). Amino acid substitutions are designated for instant by "S9G", which means that Ser in position 9 is replaced by Gly.

VERO-Derived Dengue Serotype 1 Viruses (VDV1)

The composition of the previously developed dengue-1 vaccine candidate LAV1 was improved by a sanitization process.

The VERO-Derived Dengue serotype 1 viruses (VDV1) disclosed herein use the DEN-1 16007 virus attenuated by serial passages on PDK cells. VDV1 contains the whole genomic sequence of the live-attenuated DEN-1 virus, and bears the same spots which have been linked to attenuation as the original LAV1 strain that was tested in humans.

Sanitization of the LAV1 vaccine candidate was performed by removing proteins and introducing only purified viral genomic material into Vero cells. More specifically, sanitization of the strain was performed in 2 steps:

1) Amplification of DEN16007/PDK11 (LAV1/PDK11) on Vero cells, at 32° C.

2) Purification and transfection of viral RNA into Vero cells.

Step 1 has been carried out by one passage of LAV1/PDK11 on Vero cells. For that purpose, Vero cells were infected with LAV1/PDK11 at a moi of 0.01 and incubated at 32° C. for 5 days.

For step 2, advantage was taken of the fact that the viral genome is an infectious RNA, which means that it is able, when introduced into a cell, to reconstitute a complete infectious virus. The second purification and transfection step thus comprised the steps consisting of:

a) extracting and purifying viral RNA from plaque-purified viruses;

b) advantageously associating of the purified RNA with cationic lipids;

c) transfecting Vero cell, in particular Vero cell LS10;

d) recovering of the neo-synthesized viruses; and e) purifying a VDV strain by plaque purification and optionally amplifying it in host cells, especially Vero cells.

The Vero cell technology is a well-known technology which has been used for different commercial products (injectable and oral polio vaccines, rabies vaccine). In the present invention qualified Vero cells were advantageously used to guarantee the absence of any risks potentially linked to the presence of adventitious agents. By "qualified VERO cells" is meant cells or cell lines for which culture conditions are known and is such that the said cells are free from any adventitious agents. These include e.g. the VERO cell LS10 of Sanofi Pasteur.

The thus isolated VDV strains are classically stored either in the form of a freezed composition or in the form of a lyophilised product. For that purpose, the VDV can be mixed with a diluent classically a buffered aqueous solution comprising cryoprotective compounds such a sugar alcohol and stabilizer. The pH before freezing or lyophilisation is advantageously settled in the range of 6 to 9, e.g. around 7 such as a pH of 7.5+/−0.2 as determined by a pH meter at RT. Before use, the lyophilised product is mixed with a pharmaceutically diluent or excipient such as a sterile NaCl 4% solution to reconstitute a liquid immunogenic composition or vaccine.

Sequencing, at attenuation-specific loci, of virus recovered after transfection, did not reveal any mutation, compared to the LAV1/PDK13 strain. The biologically cloned VDV1 virus exhibits a homogenous plaque phenotype and a remarkable genetic stability with regard to its LAV1 parent as it can be deduced especially from the conservation of the attenuation genotype.

VDV1 strain was sequenced and compared with the serotype 1 Dengue Live Attenuated Virus (LAV1/PDK13) strain sequence (SEQ ID No 3). A set of 3 nucleotide differences was found with regard to the reference LAV1 sequence. One of them is silent at the amino acid level (position 2719). The two others (positions 5962 and 7947) are located in non-structural peptides coding sequences (NS3-481 and NS5-125, respectively). None of these differences corresponds to any of the LAV1 attenuation positions.

The invention thus provides for live attenuated dengue-1 virus strains that have been obtained from the wild type virus DEN-1 16007 attenuated by serial passages on PDK cells and then by passage and sanitization on VERO cells. In particular the attenuated strains of the invention comprise at least the identified sequence mutations (non-silent and optionally silent) relative to the nucleotide sequence or polyprotein sequence of the wild-type DEN-1 16007 and LAV1/PDK13 strains.

Accordingly, the invention relates to an isolated live attenuated dengue-1 virus strain which comprises, or consists of, the sequence of LAV1/PDK13 strain (SEQ ID No.3) wherein at least nucleotides at positions 5962 and 7947, and optionally 2719, are mutated, with the proviso that the following nucleotides are not mutated: 1323, 1541, 1543, 1545, 1567, 1608, 2363, 2695, 2782, 5063, 6048, 6806, 7330, and 9445. Preferably, the mutations are substitutions. Preferably, the nucleotide at position 5962 is A, the nucleotide at position 7947 is G. Still preferably, the isolated strain according to the invention contains sequence SEQ ID No.3 which comprises the mutations 2719 G>A, 5962 C>A, and 7947 A>G.

Hence, a live attenuated dengue-1 virus strain according to the invention comprises the sequence of wild-type dengue-1 strain 16007 (SEQ ID No.2) wherein said sequence comprises at least the mutations 1323 T>C, 1541 G>A, 1543 A>G, 1545 G>A, 1567 A>G, 1608 C>T, 2363 A>G, 2695 T>C, 2782 C>T, 5063 G>A, 5962 C>A, 6048 A>T, 6806 A>G, 7330 A>G, 7947 A>G, and 9445 C>T. Preferably, a live attenuated strain according to the invention further comprises the mutation 2719 G>A by reference to the nucleotide sequence of wild-type strain 16007 (SEQ ID No.2).

The live attenuated dengue-1 virus strains according to the invention encompass variant strains that comprise a sequence SEQ ID No.3 mutated in positions 5962 and 7947, as defined above, and that further comprise a substitution of one or more nucleotides in a given codon position that results in no alteration in the amino acid encoded at that position.

Advantageously, the live attenuated dengue-1 virus strain according to the invention comprises a sequence which differs by a limited number of mutations, e.g. no more than 5, still preferably no more than 2, from SEQ ID No.1.

Preferably, the genomic sequence of a dengue-1 virus strain according to the invention consists of the nucleotide sequence SEQ ID No.1.

The invention also relates to live attenuated dengue-1 strains that may be derived from the VDV1 strain of sequence SEQ ID No.1 by further passages on cells, in particular Vero cells.

The invention also relates to an isolated nucleic acid which comprises, or consists of, the DNA sequence SEQ ID No.1 or its equivalent RNA sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, by RNA sequence "equivalent" to SEQ ID No.1 is meant a sequence SEQ ID No.1 wherein deoxythymidines have been replaced by uridines. As SEQ ID No.1 constitutes VDV1 cDNA sequence, the equivalent RNA sequence thus corresponds to the positive strand RNA of VDV1.

The invention further relates to the polyprotein of sequence SEQ ID No.41 and to fragments thereof. SEQ ID No.41 is the sequence of the polyprotein encoded by SEQ ID No.1

A "fragment" of a reference protein is meant a polypeptide which sequence comprises a chain of consecutive amino acids of the reference protein. A fragment may be at least 8, at least 12, at least 20, amino acid long.

Said fragments of the polyprotein of sequence SEQ ID No.41 comprise at least a lysine at position 481 of NS3 protein (position 1956 of SEQ ID No.41), and/or an arginine at position 125 of NS5 protein (position 2618 of SEQ ID No.41).

According to an embodiment the fragment of the polyprotein encoded by SEQ ID No.1 is or comprises NS3 protein and/or NS5 protein.

Immunogenic and Vaccine Compositions

The invention also relates to an immunogenic composition, suitable to be used as a vaccine, which comprises a VDV1 strain according to the invention.

The immunogenic compositions according to the invention elicit a specific humoral immune response toward the dengue virus comprising neutralizing antibodies.

Preferably, the immunogenic composition is a vaccine.

According to an embodiment, the immunogenic is a monovalent composition, i.e. it elicits a specific immune response and/or confers protection against Dengue-1 virus only.

According to another embodiment, the invention relates to a multivalent dengue immunogenic composition. Such a multivalent immunogenic composition or vaccine may be obtained by combining individual monovalent dengue vaccines. The immunogenic or vaccine composition may further comprise at least a live attenuated dengue virus of another serotype. In particular, the immunogenic or vaccine composition may comprise a VDV1 according to the invention in combination with at least a live attenuated dengue virus selected from the group consisting of serotype 2, serotype 3, and serotype 4.

Preferably, the immunogenic or vaccine composition may be a tetravalent dengue vaccine composition, i.e. a vaccine composition that comprises a VDV1 according to the invention in combination with a live attenuated dengue-2 virus strain, a live attenuated dengue-3 virus strain and a live attenuated dengue-4 virus strain.

Live attenuated dengue-2, dengue-3 and dengue-4 virus strains have been described previously. Reference may be made to the live-attenuated vaccines that were developed by Mahidol University by passaging dengue serotype 2 (strain 16681, passage 53; LAV2), and serotype 4 (strain 1036, passage 48, LAV4) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3) (LAV3). The nucleotide sequences of LAV2 (SEQ ID No.42), LAV3 (SEQ ID No.43), and LAV4 (SEQ ID No.44) are shown in the annexed sequence listing.

Advantageously, a live attenuated dengue-2 strain may correspond to a VDV2 strain which has been obtained from the LAV2 strain developed by Mahidol by a process of sanitization on Vero cells. In particular a live attenuated dengue-2 strain (VDV2) may comprise, and advantageously consists of the sequence SEQ ID No.40.

Immunogenic compositions including vaccines may be prepared as injectables which can correspond to liquid solutions, suspensions or emulsions. The active immunogenic ingredients may be mixed with pharmaceutically acceptable excipients which are compatible therewith.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Preferably, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the VDV1 strain. Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a dengue infection which comprises administering the host with an immunoeffective amount of an immunogenic composition or a vaccine according to the invention.

A "host in need thereof" denotes a person at risk for dengue infection, i.e. individuals travelling to regions where dengue virus infection is present, and also inhabitants of those regions.

The route of administration is any conventional route used in the vaccine field. The choice of administration route depends on the formulation that is selected. Preferably, the immunogenic composition or vaccine corresponds to an injectable composition administered via subcutaneous route, advantageously in the deltoid region.

The amount of LAV or VDV in particular VDV1 in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or from $10^3$ to $10^5$ $CCID_{50}$ of LAV or VDV, for instance 4±0.5 $\log_{10}$ $CCID_{50}$ of VDV1 strain for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralizing antibodies in the serum of a vaccinee, as evaluated by the plaque reduction neutralization test as described in section 4.1.2.2; a serum being considered to be positive for the presence of neutralizing antibodies when the neutralizing antibody titer thus determined is at least superior or equal to 1:10.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naïve as well as well as non-naïve with regards to dengue virus. The vaccines of the invention can be administered in a single dose or, optionally, administration can involve the use of a priming dose followed by a booster dose that is administered, e.g. 2-6 months later, as determined to be appropriate by those of skill in the art.

The invention will be further described in view of the following figures and examples.

FIGURES

Figure 3:
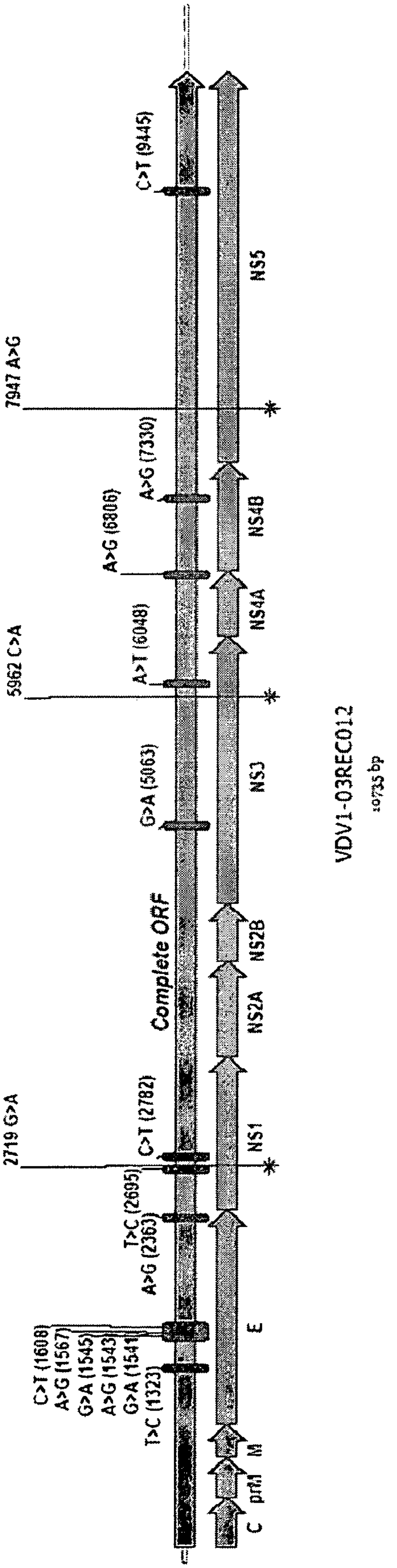

FIG. 3 is a diagrammatic representation of VDV1 genome map. The above arrow is the polyprotein coding sequence. The below arrows represent mature peptides coding sequence. The vertical bars symbolize the nucleotidic variations between wild-type dengue 1 strain 16007 and LAV1 strain. The stars designate the nucleotidic variations between LAV1 and VDV1.

Figure 4:
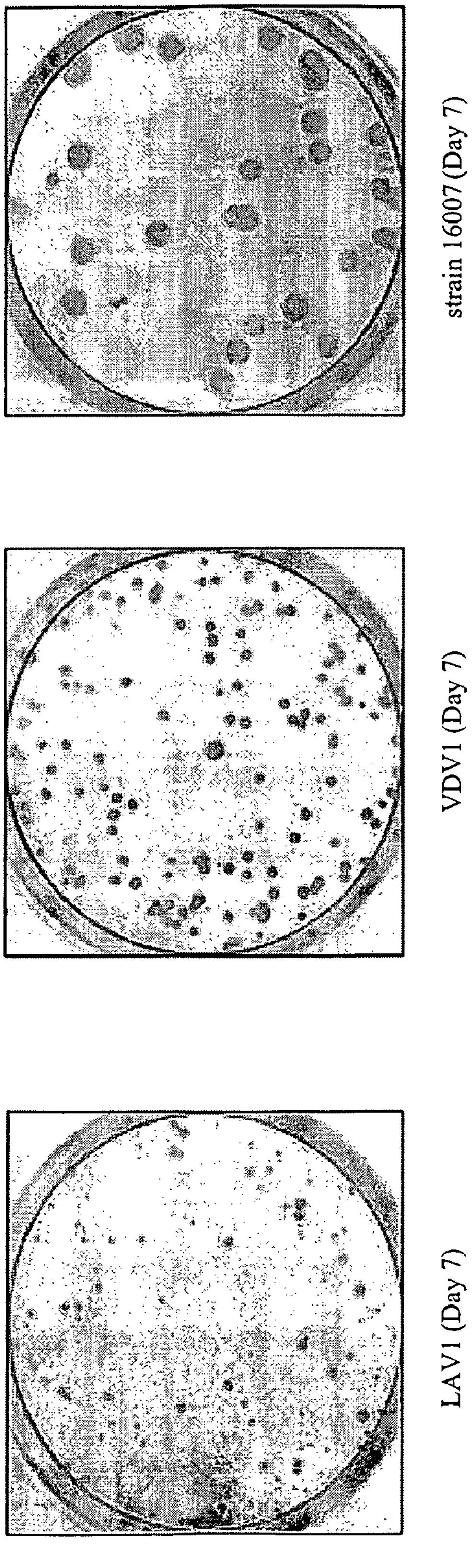

FIG. 4 shows plaque size analysis after 7 days of incubation at 37° C. for dengue-1 viruses LAV1, VDV1, and strain 16007.

Figure 5:
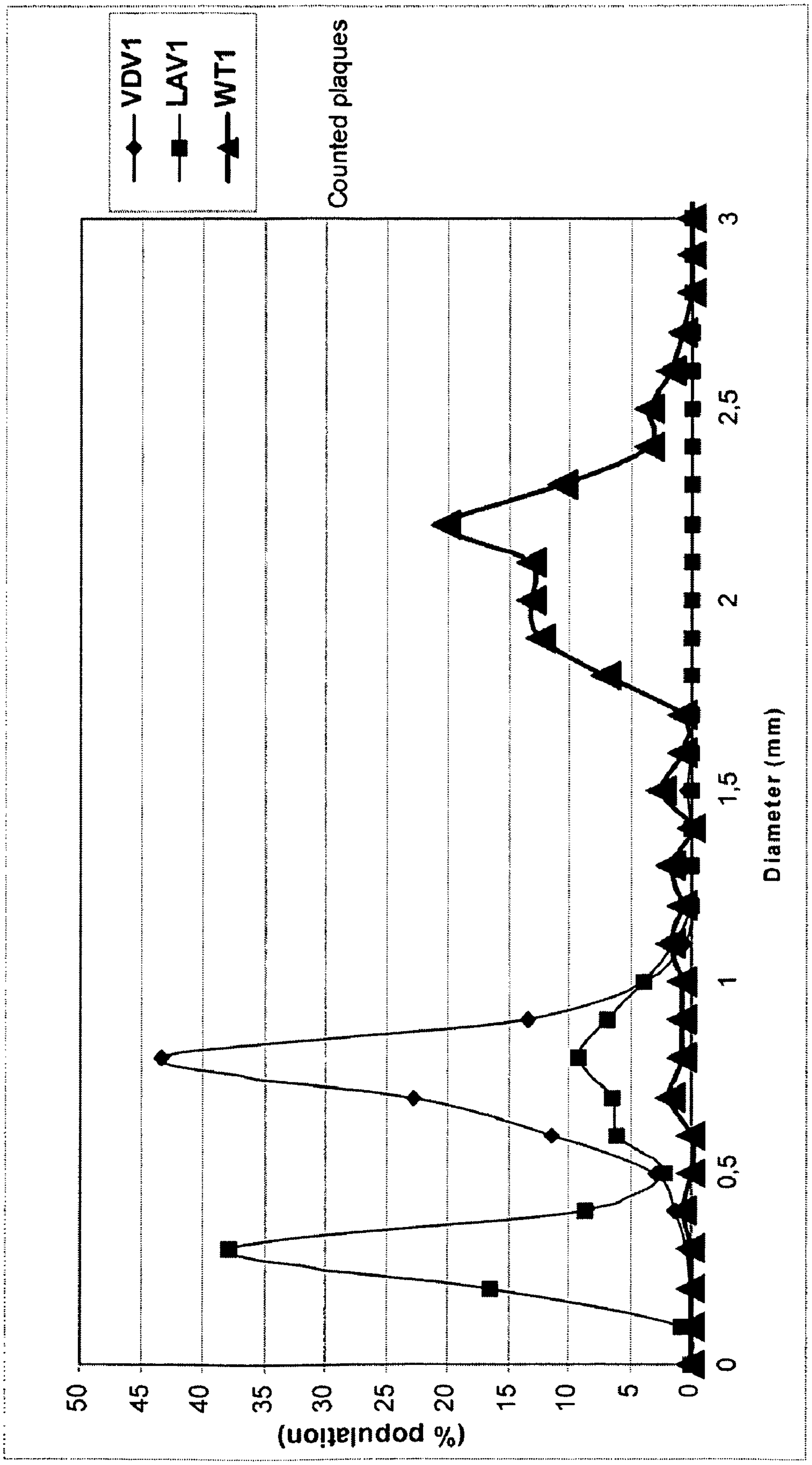

FIG. 5 is a graphic analysis showing plaque size distribution for dengue-1 viruses LAV1, VDV1, and strain 16007.

Figure 6:
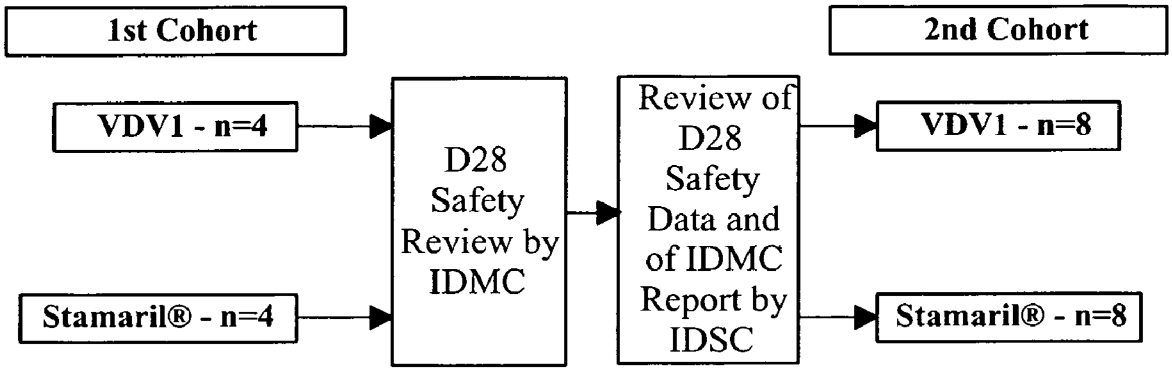

FIG. 6 is a summary of Trial Design for assessment of safety of VDV1 monovalent in healthy flavivirus-naïve adults.

EXAMPLES

Example 1

Sanitization 1.1 Viral RNA Purification

It was initially intended to perform sanitization of LAV1 by purifying and transfecting viral RNA directly extracted from an early seed of the vaccine strain, DEN-16007/PDK10 or DEN-16007/PDK11 (produced by Sanofi Pasteur. Titer: 4.60 $logTCID_{50}$/ml). Eight unsuccessful assays were carried out in that way, with RNA quantities varying from $10^3$ to $10^7$ copies. It was then decided to perform one adaptation passage on Vero cells, before RNA extraction and transfection.

Vero cells (VERO LS10 p142 to 145) were infected with a sample of the master seed DEN-1/PDK11, at m.o.i 0.01, and incubated at 32° C. for 5 days. Culture medium was then replaced by infection medium (containing 10 mM $MgSO_4$). Clear cytopathic effects were visible the following day, and presence of viral RNA in culture supernatant was confirmed by RT-PCR. Culture medium was collected at day 8 post-infection, diluted with an equivalent volume of an aqueous buffered solution comprising cryoprotective agents (pH=7.5) and kept frozen at −70° C. until use. This Vero-amplified virus was named DEN-1/V100. Its infectious titer was determined on Vero cells and was of 6.9 $logTCID_{50}$/ml.

The RNA purification and transfection process was performed as follows. DEN-1 V100 suspension was diluted in order to contain at least $3\times10^4$ and up to $3\times10^7$ $TCID_{50}$ or PFU of virus per milliliter. One unit of benzonase diluted in 0.01 ml of William's medium was added to 0.5 ml of virus, in order to digest DNA or RNA molecules from cellular origin, and the solution was incubated for 2 hours at 4° C. on an agitator. At the end of incubation step, 0.65 ml of a denaturing buffer containing guanidium chloride, detergent (SDS), and βmercaptoethanol (RTL-βmercaptoethanol buffer, provided in the kit RNeasy Mini kit, Qiagen Ref. 74104) were added and proteins were extracted once with phenol/chloroform (1/1) vol/vol and once with chloroform vol/vol, followed by centrifugation for 5 min at 14,000 rpm at room temperature. After each extraction, the aqueous phase was collected, taking care not to collect material (white precipitate) at the interface, and transferred to a clean 1 ml-Eppendorf tube. The RNA solution was then applied onto a QIAgen column following the recommendations of the manufacturer (RNeasy minikit, QIAgen), in order to remove traces of solvent, and eluted with 0.06 ml of nuclease-free H2O water. The presence of viral RNA was confirmed by quantitative RT-PCR, using a reference curve established with known quantities of virus, in $TCID_{50}$/ml.

1.2 Transfection of Vero Cells with Purified RNA

Transfection was performed using lipofectamine (LF2000 Reagent, Life Technologies), a mixture of cationic lipids that associate to RNA through charge interactions and allows transfer of the complexes into the cytoplasm of the cells by fusion with the cell membrane. The optimal quantity of LF2000 reagent was determined in a preliminary experiment by incubating Vero cells, plated 16 to 24 hours before (0.3-$0.5\times10^6$ cells per well in a 6 wells plate) with increasing doses (5 to 20 μl) of lipofectamine. Cells were then incubating 4 to 5 hours at 32° C., 5% $CO_2$, before replacing the medium by fresh culture medium without FCS, and the incubation was continued overnight at 32° C. Toxicity (round, refringent or floating cells, homogeneity of the cell monolayer) was checked regularly for 48 hours, under an inverted microscope. The highest dose of lipofectamine that was not toxic under these conditions was 10 μl and was chosen for RNA transfection.

Four transfections were carried out in parallel, using 1/10 of the purified RNA preparation (corresponding to about $4\times10^5$ $TCID_{50}$). Twelve microliters of viral RNA solution were diluted in 500 μl of OptiMEM medium (GIBCO) containing 10 μl of LF2000 Reagent (a mixture of cationic lipids that associate to RNA through charge interactions, and allow transfer of the complexes into the cytoplasm of the cells by fusion with the cell membrane). 200 ng of yeast tRNA were added as carrier in 2 out of the 4 reactions.

The 4 transfection mixes were allowed to precipitate for 10 min at room temperature before addition to 6-wells plates of confluent Vero cells. After 4 hours of incubation at 32° C., transfection mix was removed and cells were rinsed once in PBS. Three milliliters of post-transfection medium (Williams, GIBCO) were added, and incubation was continued for 5 days at 32° C. Culture medium was then replaced by 3 ml of Dengue infection medium (Williams supplemented with 10 mM $MgSO_4$).

Moderate toxic effects were observed 24 hours post-transfection and disappeared on day 3. Typical cytopathic effects (round, refringent cells) were detected 6 to 8 days post-transfection in all transfection assays. Release of virus in the supernatant of these cells was confirmed by qRT-PCR. Culture fluids (3 ml) were collected at day 6 and at day 8 post-transfection, and pooled. The viruses were diluted with 6 ml of an aqueous buffered solution comprising cryoprotective agents (pH=7.5) and frozen until further amplification.

The four viral solutions such obtained after transfection were named TV (for Transfection in Vero cells) 100, TV200, TV300 and TV400, and exhibited similar infectious titers (see below):

TV100: 6.95 log $TCID_{50}$

TV200: 6.80 log $TCID_{50}$

TV300: 6.80 log $TCID_{50}$

TV400: 6.85 log $TCID_{50}$

Of note, transfection efficiency was not significantly increased in samples transfected in presence of tRNA (TV300 and TV400).

1.3 Characterization of Viruses Recovered After Transfection

Plaques sizes of DEN1-V100 and TV100 to 400 were determined. Briefly, Vero cells were plated at a density of 1.000.000 cells/$cm^2$ in culture medium containing 4% of FBS. After overnight incubation, the medium was removed and cells were infected with serial twofold or fivefold dilutions of virus. After 1.5 hour at 37° C. 5% $CO_2$, the inoculum was removed and cells were incubated at 37° C. 5% $CO_2$ in Minimal Eagle Medium (MEM) containing 1.26% methylcellulose and 10% FBS. After 11 days of incubation, plates were fixed 20 minutes in cold acetone at −20° C. and revealed by immuno-coloration with a flavivirus-specific mAb, diluted at 2.5 μg/ml. Viral plaques were measured using an image analysis software (Saisam/Microvision)

As a control, DEN-1 16007 and LAV1 were plated in parallel. The data are presented in Table 1.

TABLE 1

Plaques size of DEN-1 16007, LAV1, V100 (before transfection) and TVX00 (after transfection)

| | | Phenotype | |
|---|---|---|---|
| Step | Virus | Large Plaque | Small Plaque |
| | DEN1 16007 (wt) | 42 | 0 |
| Master Seed/PDK11 | MS-16007/PDK11 | 0 | 91 |
| Working Seed/PDK12 | WS LST-22 | 0 | 84 |
| Bulk Seed/PDK13 | D1-0010R1 | 0 | 188 |
| VERO amplification | V100 | 0 | 90 |
| Transfected viruses | TV100 | 0 | 115 |
| | TV200 | 1 | 90 |
| | TV300 | 0 | 92 |
| | TV400 | 0 | 107 |

The V100 virus, amplified on Vero cells, exhibits a homogeneous small plaque (SP) phenotype. Plaques are slightly larger than observed in the different samples of LAV1 (2-3 mm diameter instead of <2 mm). This SP phenotype is retained in the viruses recovered after transfection. One large plaque (LP), among 90 virus plated, was detected in TV200 sample. However, this proportion shifted to 10 LP for 82 SP plated after just one amplification passage on VERO cells suggesting that the LP population was dominant.

Of note, sequencing of attenuation-critical positions performed in parallel did not reveal any mutation in transfected viruses, compared to LAV1.

1.4 Plaque-Purifications

A sample of DEN-1/TV100 virus, presenting a homogenous SP phenotype was chosen for plaque-purification. Briefly, Vero cells were plated in 6-well plates and infected with serial dilutions of virus, in order to get between 1 and 20 plaques by plate. After 1.5 hour at 37° C. 5% $CO_2$, the inoculum was removed and cells were incubated under 3 ml of solid medium composed of MEM-10% FCS pre-heated at 42° C. and mixed extemporaneally with 2% of melted agarose equilibrated at 42° C. The medium was allowed to solidify at room temperature for 30 min; under flow hood, and plates were incubated in inverted position for 10 days at 32° C.-5% $CO_2$. A second layer of the same medium supplemented with 0.01% of neutral red was then added and plates were incubated for an additional night at 32° C. Four well-isolated small plaques were picked under sterile conditions using a micro-pipet equipped with a 0.1 ml tip, and transferred into sterile tubes containing 0.2 ml of MEM-4% FCS. The suspension was homogenized by vortexing, serially diluted in the same medium, and immediately used to infect 6-well plates of Vero cells. The protocol was repeated and a second picking of six SP was done. Each picked plaque was diluted in 1 ml of medium, before amplification on Vero cells, in T25 $cm^2$ flasks. Culture medium was collected at day 6 post-infection, diluted with the same volume of an aqueous buffered solution comprising cryoprotective agent (pH 7.5) and frozen at −70° C. All these steps were performed at 32° C.

Plaque-purified viruses were named DEN-1/TV111, DEN-1/TV112, DEN-1/TV121, DEN-1/TV131, DNE-1/TV132 and DEN-1/TV141, respectively. Infectious titers were determined on Vero cells (see below):

TV111=6.85 $LogCCID_{50}$/ml TV112=6.80 $LogCCID_{50}$/ml

TV121=6.80 $LogCCID_{50}$/ml TV131=6.70 $LogCCID_{50}$/ml

TV132=6.45 $LogCCID_{50}$/ml TV141=5.70 $LogCCID_{50}$/ml

A second amplification on Vero cells was carried out for three clones: TV111, TV112 and TV121.

1.5 Characterization of Cloned Virus

Plaques size of DEN-1/TV111, DEN-1/TV112, DEN-1/TV121, DEN-1/TV131, DEN-1 TV132 and DEN-1/TV141 candidates were determined. Spot-sequencing of specific attenuation loci was also performed and revealed no mutation (Table 2).

TABLE 2

Sequencing at attenuation-specific spots of DEN-1 viruses

| Step/cell | Virus | E 1323 | E 1541 | E 1543 | E 1545 | E 1567 | E 1608 | E 2363 | NS1 2695 | NS1 2782 | NS3 5063 | NS3 6048 | NS4A 6806 | NS4B 7330 | NS5 9445 |
|---|---|---|---|---|---|---|---|---|---|---|---|---|---|---|---|
| Non attenuated/ PGMK | DEN-1 16007 | T | G | A | G | A | C | A | G | C | G | A | A | A | C |
| Vaccine/PDK | DEN-1 16007/ PDK-13 | C | A | G | A | G | T | G | C | T | A | T | G | G | T |
| | TV111 | C | A | G | A | G | T | G | C | T | A | T | G | G | T |
| | TV112 | C | A | G | A | G | T | G | C | T | A | T | G | G | T |
| 2nd plaque-purification/ VERO | TV121 | C | A | G | A | G | T | G | C | T | A | T | G | G | T |
| | TV131 | C | A | G | A | G | T | G | C | T | A | T | G | G | T |
| | TV132 | C | A | G | A | G | T | G | C | T | A | T | G | G | T |
| | TV141 | C | A | G | A | G | T | G | C | T | A | T | G | G | T |
| Pre-master seed/VERO | VDV1 (VERO-6) | C | A | G | A | G | T | G | C | T | A | T | G | G | T |

Nucleotides position are indicated below each gene and referred of DEN-1 16007 strain SEQ ID No 2.

In absence of any other criterion able to differentiate between these clones, TV121 was arbitrarily chosen as pre-master for VDV1.

In conclusion, a total number of 6 passages on VERO cells were carried out to adapt and clone the initial DEN-1 16007/PDK11 attenuated strain. Viral RNA was purified and transfected into qualified VERO cells, in conditions fitting with an industrial application (environmental control, traceability of raw material and experiments, certificate of analysis for animal-derived products). The VERO-adapted strain was cloned by plaque-purification to generate pre-master seed of VDV1 vaccine candidate, at VERO passage number 6.

Contrary to LAV1, VDV1 presents a homogenous small plaque size phenotype. Furthermore, no mutation was identified at attenuation-specific positions. Further characterizations have been performed then by determining bulk VDV1 complete sequence and phenotypic testing.

Example 2

Sequencing

The complete sequence of the virus was generated according to the following strategy. Starting from a VDV1-containing sample, the genomic RNA was extracted and purified, retro-transcribed into cDNA. Then all overlapping PCR amplifications were performed from the cDNA, with addition of the sequencing tags at both ends of each PCR product. All individual sequences were generated in automated devices and analysed. Next step consisted of the genome reconstruction by multiple alignments of all individual sequences. At this point, each unexpected nucleotide change, with regard to the reference sequence, was carefully re-analysed by going back to raw data. Such change was systematically confirmed by another sequence performed from a new PCR product. Once all ambiguities were solved, the sequenced virus genome was completed, and the new molecule was created in Vector NTi database. It can be used for inter genomes analysis, by multiple sequence alignment.

2.1 Materials 2.1.1 Viruses

The viruses to which it is referred here are DEN-1 16007; LAV-1/PDK13; VDV1, the sequences of which are given in the attached sequence listing. The complete genome sequence of these viruses is 10735 nucleotides in length.

2.1.2 Primers

All primers have been designed in Seqweb bioinformatics package (Accelrys), primer design module (Table 3).

TABLE 3 list of RT-PCT and sequencing primers

| Name | Primers sequences | | NtStart | NtEnd | Primer length | RT-PCR length | Overlap |
|---|---|---|---|---|---|---|---|
| D1 01+ | GTTTTCCCAGTCACGACtacgtggaccgacaagaacag | (SEQ ID No. 4) | 12 | 32 | 38 | 897 | -32 |
| D1 01- | AACAGCTATGACCATGggatggagttaccagcatcag | (SEQ ID No. 5) | 928 | 908 | 37 | | 201 |
| D1 02+ | GTTTTCCCAGTCACGACtgaacaccgacgagacaaac | (SEQ ID No. 6) | 688 | 707 | 37 | 892 | 173 |
| D1 02- | AACAGCTATGACCATGaggtccaaggcagtggtaag | (SEQ ID No. 7) | 1598 | 1579 | 36 | | |
| D1 03+ | GTTTTCCCAGTCACGACttggaaatgagaccacagaac | (SEQ ID No. 8) | 1386 | 1406 | 38 | 885 | 146 |
| D1 03- | AACAGCTATGACCATGgaaacaccgctgaacaaaac | (SEQ ID No. 9) | 2289 | 2270 | 36 | | |
| D1 04+ | GTTTTCCCAGTCACGACggttcaagaagggaagcag | (SEQ ID No. 10) | 2106 | 2124 | 36 | 903 | 183 |

TABLE 3-continued list of RT-PCT and sequencing primers

| Name | Primers sequences | | NtStart | NtEnd | Primer length | RT-PCR length | Overlap |
|---|---|---|---|---|---|---|---|
| D1 04− | AACAGCTATGACCATGttctatccagtaccccatgtc | (SEQ ID No. 11) | 3028 | 3008 | 37 | | |
| D1 05+ | GTTTTCCCAGTCACGACcagaataccaccttcatcatcg | (SEQ ID No. 12) | 2804 | 2825 | 39 | 868 | 232 |
| D1 05− | AACAGCTATGACCATGttcccatccccatcttgtc | (SEQ ID No. 13) | 3689 | 3671 | 35 | | |
| D1 06+ | GTTTTCCCAGTCACGACggaaatcagaccagtcaaggag | (SEQ ID No. 14) | 3418 | 3439 | 39 | 913 | 233 |
| D1 06− | AACAGCTATGACCATGtgttgtgtgaggcaccagag | (SEQ ID No. 15) | 4349 | 4330 | 36 | | |
| D1 07+ | GTTTTCCCAGTCACGACgcaaaccactaaccatgtttc | (SEQ ID No. 16) | 4077 | 4097 | 38 | 901 | 259 |
| D1 07− | AACAGCTATGACCATGccacttgttgtcaccactc | (SEQ ID No. 17) | 4995 | 4977 | 35 | | |
| D1 08+ | GTTTTCCCAGTCACGACcccaagggaagagactggaac | (SEQ ID No. 18) | 4699 | 4718 | 37 | 908 | 210 |
| D1 08− | AACAGCTATGACCATGtcctgatttgatgcttggaac | (SEQ ID No. 19) | 5626 | 5606 | 37 | | |
| D1 09+ | GTTTTCCCAGTCACGACaagcacattttaccgatccag | (SEQ ID No. 20) | 5376 | 5396 | 38 | 900 | 182 |
| D1 09− | AACAGCTATGACCATGgtcgtagtttctttctttctccttc | (SEQ ID No. 21) | 6299 | 6275 | 41 | | |
| D1 10+ | GTTTTCCCAGTCACGACgcaatagacggggaatacag | (SEQ ID No. 22) | 6074 | 6093 | 37 | 809 | 138 |
| D1 10− | AACAGCTATGACCATGatgatggtggttttcagcag | (SEQ ID No. 23) | 6901 | 6882 | 36 | | |
| D1 11+ | GTTTTCCCAGTCACGACgtgttgcttattccagagcc | (SEQ ID No. 24) | 6725 | 6744 | 37 | 877 | 228 |
| D1 11− | AACAGCTATGACCATGgctgtcttttccatttttctcc | (SEQ ID No. 25) | 7622 | 7601 | 38 | | |
| D1 12+ | GTTTTCCCAGTCACGACactttgcacatcacagatcc | (SEQ ID No. 26) | 7354 | 7373 | 37 | 821 | 175 |
| D1 12− | AACAGCTATGACCATGttcgcactagcattcctcc | (SEQ ID No. 27) | 8192 | 8174 | 35 | | |
| D1 13+ | GTTTTCCCAGTCACGACcacctgagaaatgtgacacc | (SEQ ID No. 28) | 7980 | 7999 | 37 | 907 | 207 |
| D1 13− | AACAGCTATGACCATGtttccttgtttatgaagctccc | (SEQ ID No. 29) | 8907 | 8886 | 38 | | |
| D1 14+ | GTTTTCCCAGTCACGACcaaaagcgaaacgaggcac | (SEQ ID No. 30) | 8661 | 8679 | 36 | 894 | 221 |
| D1 14− | AACAGCTATGACCATGgtttcaccacacagtcatctcc | (SEQ ID No. 31) | 9575 | 9554 | 38 | | |
| D1 15+ | GTTTTCCCAGTCACGACagaccagcgaaaaatggaac | (SEQ ID No. 32) | 9314 | 9333 | 37 | 865 | 262 |
| D1 15− | AACAGCTATGACCATGtcccaatgagccttctcac | (SEQ ID No. 33) | 10196 | 10178 | 35 | | |
| D1 16+ | GTTTTCCCAGTCACGACgctaatgctatctgttcagcc | (SEQ ID No. 34) | 9896 | 9916 | 38 | 812 | |
| D1 16− | AACAGCTATGACCATGtgattcaacagcaccattcc | (SEQ ID No. 35) | 10726 | 10707 | 36 | | −28 |
| D1 16i+ | ccatggaagctgtacgc | (SEQ ID No. 36) | 10480 | 10496 | 17 | | |
| D1 16i− | gagacagcaggatctctgg | (SEQ ID No. 37) | 10671 | 10652 | 19 | | |

2.2 Methods 2.2.1 Viral RNA Purification

From previous experience, a minimal of 1000 $DICC_{50}$ is required to get a positive RT-PCR reaction in the next steps. This means that a minimum virus titer of $10^4$ $DICC_{50}$/mL is necessary. Virus genomic RNA was purified using QIAamp viral RNA mini kit (Qiagen), according to the manufacturer's recommendations. Briefly, a volume of 140 μl from a crude viral sample was incubated in the presence of the lysis solution, and loaded onto a kit column. After washing steps, the purified viral RNA was eluted by 60 μl of sterile nuclease-free water containing 1 μl (40 units) of RNAse inhibitor (RNAse Out, Sigma).

2.2.2 Reverse Transcription

Viral RNA was reverse transcribed into cDNA by a reverse transcriptase (reverse iT) from ABGene. Again, standard operating conditions were applied, using 10 μl of purified RNA, in a final reaction volume of 20 μl. The reaction was initiated by hybridization of the minus strand primers. One RT reaction per PCR was performed (Table 1). The cDNA synthesis was obtained by 45 min incubation at 47° C.

2.2.3 PCR

All PCR were performed with Expand High Fidelity PCR system (Roche diagnostics), using all 16 pairs of primers (+) and (−) from Table 1. PCR conditions were the following ones:

| | | |
|---|---|---|
| RT | 2 | μl |
| 10 × buffer | 2.5 | μl |
| dNTP mix (10 mM) | 2 | μl |
| Primers | 0.8 | μl each |
| H2O | 16.4 | μl |
| Enzyme | 0.5 | μl |

PCR program

| | | | |
|---|---|---|---|
| Denaturation | 94° C. | 2 min | |
| Denaturation | 94° C. | 15 sec | 40 cycles |
| Hybridization | 55° C. | 30 sec | 40 cycles |
| Elongation | 68° C. | 1 min | 40 cycles |
| Elongation | 68° C. | 5 min | |

All PCR products were controlled by electrophoresis on agarose gel.

2.2.4 Sequencing

The major part of the sequence reactions has been outsourced to Genome Express. Genome extremities, ambiguities, some inter-PCR junctions, and regions not sequenced by Genome Express for technical reasons were performed in-house.

- Sequencing at Genome Express: PCR products were shipped at +4° C., and sequencing results were received as informatic sequence files. Text file, quality files and chromatograms are available for each individual sequence. After sequence alignment, all discrepancies were checked on the chromatogram, and corrected if identified as sequence algorithm errors.
- In-house sequencing: Sequence reactions were performed on thermocycler PTC-200 (MJ Research), with Sequitherm Excell II LC kit (Epicentre). Each PCR product was sequenced on both strands independently in a single reaction. Reactions were loaded onto a sequence electrophoresis gel. Run and analysis of sequence were performed on the automated sequencer Gene ReadIR 4200 (Li-Cor).

| | | |
|---|---|---|
| DNA | up to 200/250 | ng |
| Reaction buffer | 7.2 | μl |
| Primers (1-2 pM) | 1.5 | μl each |
| Enzyme | 1 | μl |
| H2O | up to 20 | μl |

PCR program

| | | | |
|---|---|---|---|
| Denaturation | 92° C. | 2 min | |
| Denaturation | 92° C. | 15 sec | 30 cycles |
| Hybridization | 50° C. | 30 sec | 30 cycles |
| Elongation | 70° C. | 1 min | 30 cycles |
| Elongation | 70° C. | 10 sec | |

Denaturation of samples 3 min at 95° C. and ice cooling just before samples loading.

| Electrophoresis parameters | | Gel parameters | |
|---|---|---|---|
| Voltage | 1500 V | Gel hight | 41 cm |
| Current | 35 mA | Gel thickness | 0.2 mm |
| Power | 40 W | Temperature | 45° C. |
| Run time | 9H00 | Scan speed | 3 |

2.3 Results

All PCR fragments were sequenced from both ends using a common PCR added tail, i.e. a specific motif which has been added at 5' end of all primers:

```
5' primers:
M13SEQ-GTTTTCCCAGTCACGAC     (SEQ ID No. 38)

3' primers:
M13REV-AACAGCTATGACCATG      (SEQ ID No. 39)
```

M13-SEQ and -REV sequences correspond to universal M13 primers motifs (New England Biolabs references).

For final contig assembly, a quick analysis was performed in Vector NTi, in ContigExpress module (Informax). The LAV1 reference sequence was compared with all individual sequencing results. In such conditions, all results could be aligned at the right place on the complete genome, even when some regions were still missing contig assembly, giving a quick visualization of the overall genome alignment.

2.3.1 Complete VDV1 Sequence Assembly

The final sequence alignment was performed in Vector NTi, AlignX module (Informax). The classical multiple sequence alignment algorithm ClustalW (Thompson et al., 1994) was used by the software to build the global alignment. All the sequence results were aligned together with the LAV1 reference sequence, thus allowing for a better reconstruction of the genome. Any discrepancy in the sequence with regard to the reference required a confirmation on another independent sequence reaction. The complete sequence of VDV1 is shown in SEQ ID No.1.

Some ambiguities are often found in single sequences, especially near sequence extremities. This is inherent to the somewhat poor quality of the reaction at both ends of any PCR fragment. Such poor quality sequences were excluded from the alignment, until two other independent sequence reactions were available from other PCR products. Discrepancy towards the reference was not taken into account in the final alignment when not confirmed in at least two independent other PCR sequences matching the consensus. Conversely, any discrepancy confirmed on two independent sequences was kept in the final sequence.

Table 4 summarizes the characteristics of each individual sequence reaction, indicating start, end and length. Overlaps between adjacent PCR are also indicated, as well as differences with regard to the reference sequence in the last column.

TABLE 4

Dengue VDV1 individual sequences characteristics

| Name | Start | End | Size | Overlap | Comments |
|---|---|---|---|---|---|
| D1 01+ | 35 | 921 | 886 | 0 | |
| D1 01− | 899 | 33 | 866 | 209 | |
| D1 02+ | 712 | 1596 | 884 | | |
| D1 02− | 1569 | 713 | 856 | 196 | |
| D1 03+ | 1415 | 2277 | 862 | | |
| D1 03− | 2253 | 1400 | 853 | 160 | |
| D1 04+ | 2133 | 3027 | 894 | | 2719 G > A (NS1-100 s) |
| D1 04− | 3000 | 2117 | 883 | 212 | 2719 G > A (NS1-100 s) |
| D1 05+ | 2834 | 3681 | 847 | | |
| D1 05− | 3654 | 2815 | 839 | 247 | |
| D1 06+ | 3451 | 4332 | 881 | | |
| D1 06− | 4325 | 3434 | 891 | 243 | |
| D1 07+ | 4113 | 4987 | 874 | | |
| D1 07− | 4961 | 4089 | 872 | 245 | |
| D1 08+ | 4742 | 5564 | 822 | | |
| D1 08− | 5583 | 4742 | 841 | 183 | |
| D1 09+ | 5400 | 5916 | 516 | | |
| D1 09− | 6274 | 5758 | 516 | 197 | 5962 C > A (NS3-481 N > K); 2 sequences |
| D1 10+ | 6114 | 6868 | 754 | | |
| D1 10− | 6883 | 6077 | 786 | 135 | |
| D1 11+ | 6761 | 7504 | 743 | | |
| D1 11− | 7597 | 6733 | 864 | 217 | |
| D1 12+ | 7381 | 8034 | 653 | | 7947 A > G (NS5-125 K > R) |
| D1 12− | 8143 | 7380 | 763 | 141 | 7947 A > G (NS5-125 K > R) |
| D1 13+ | 8003 | 9730 | 727 | | |
| D1 13− | 8857 | 8002 | 855 | 182 | |
| D1 14+ | 8687 | 9472 | 785 | | |
| D1 14− | 9544 | 8675 | 869 | 200 | |
| D1 15+ | 9344 | 10170 | 826 | | |
| D1 15− | 10162 | 9399 | 763 | 253 | |
| D1 16+ | 9917 | 10261 | 344 | | 2 sequences |
| D1 16− | 10706 | 10394 | 312 | 0 | |
| D1 16i+ | 10500 | 10706 | 206 | | |
| D1 16i− | 10649 | 10204 | 455 | | |

The two extremities of the genome could not be sequenced from PCR amplification, because cDNA synthesis and PCR DNA reaction required oligonucleotides complementary to the ends of the genome. During the amplification step, these oligonucleotides are incorporated into the PCR fragment. The sequence result is that of the synthetic oligonucleotide, and not that of the virus itself. PCR from both ends of the virus genome did work properly, suggesting that the viral sequence was not significantly different from the oligonucleotide sequence (if it had been the case, PCR amplification should have failed or at least should have been of poor quality). The two extremities of the genome could not be distinguished from all other PCR amplifications. So, in the reconstructed genome (SEQ ID No.1), both genome ends were considered as identical to oligonucleotide sequences (and also identical to the reference). At 5' end, the sequence is that of nucleotides 1 to 34. At 3' end, the sequence is that of nucleotides 10707 to 10735.

2.3.2 Sequence Comparison

Direct sequence comparison between VDV1 strain and LAV1 reference shows a series of 3 nucleotides differences. Table 5 gives the complete list of these positions.

TABLE 5

Sequence comparison between LAV1 and VDV1 strains

| Nucleotides | | | Amino Acids | | | | |
|---|---|---|---|---|---|---|---|
| Nt Position | LAV1 | VDV1 | Region | AA Position | LAV1 | VDV1 | Notes |
| 2719 | G | A | NS1 | 100 | G | G | Silent |
| 5962 | C | A | NS3 | 481 | N | K | |
| 7947 | A | G | NS5 | 125 | K | R | |

Nucleotide change in position 2719 is silent at the amino acid level. The second difference in position 5962 triggers an amino acid change at NS3-481 (asparagine to lysine). Both are hydrophilic, but lysine is positively charged, whereas asparagine is not. The last difference is located in NS5 peptide, substituting lysine to arginine in position NS5-125. Such amino acid substitution is relatively conservative from a chemical point of view, both arginine and lysine residues being hydrophilic and positively charged.

TABLE 6

Search of discrepancies on other Dengue 1 strains

| Nucleotide position on VDV1 strain | Number of strains sharing the same nucleotide |
|---|---|
| 2719 | 24/40 |
| 5962 | 6/40 |
| 7947 | 1/40 |

When performing sequence alignment between all available Genbank serotype 1 Dengue genomic sequences, it appears that most of the identified differences are also present on other strains (see Table 6). One position is unique in the VDV1 strain (position 7947; NS5-125).

Thus, the full genomic sequence of a VDV1 strain of the dengue virus has been established.

Three nucleotide differences have been detected with regard to the parent LAV1 genomic sequence. VDV1 vaccine strain is derived from LAV1, through virus "sanitization" and passage from dog to monkey cells.

Differences between LAV1 and VDV1 can have several origins. First, cloning steps can elect a viral subpopulation that is not 100% identical to the major sequence previously detected in LAV1. Second, LAV1 has been produced on PDK cells, whereas VDV1 has been made on Vero cells. Such passage from dog to monkey cells potentially induces virus changes that reflect adaptation to the new cell line. Third, as for all RNA viruses, the lower viral RNA polymerase fidelity triggers a higher genomic mutation rate than DNA polymerases do.

In term of sequences only 3 differences between LAV1 and VDV1 were observed, corresponding to only 2 amino acids substitutions. All 14 nucleotide positions that have been linked to LAV1 viral attenuation are conserved in VDV1. Furthermore the sequences of master and bulk VDV1 have been compared (Table 7).

TABLE 7

Dengue 1 nucleotide differences between wild type 16007 strain and attenuated LAV1/PDK13 and VDV1 strains

| Virus | 1323/ E-130 | 1541-3/ E-203 | 1545 E-204 | 1567/ E-211 | 1608/ E-225 | 2363/ E-477 | 2695/ NS1-92 | 2719/ NS1-100 |
|---|---|---|---|---|---|---|---|---|
| DEN-1 | T | GaA | G | A | C | A | T | G |
| 16007 | Val | Glu | Arg | Gln | Ser | Met | Asp | Gly |
| LAV1/ | C | AaG | A | G | T | G | C | G |
| PDK13 | Ala | Lys | Lys | Gln | Leu | Val | Asp | Gly |
| VDV1 | C | AaG | A | G | T | G | C | **A** |
| Master | Ala | Lys | Lys | Gln | Leu | Val | Asp | **Gly** |
| VDV1 | C | AaG | A | G | T | G | C | **A** |
| Bulk | Ala | Lys | Lys | Gln | Leu | Val | Asp | **Gly** |

| Virus | 2782/ NS1-121 | 5063/ NS3-182 | 5962/ NS3-481 | 6048/ NS3-510 | 6806/ NS4a-144 | 7330/ NS4b-168 | 7947/ NS5-125 | 9445/ NS5-624 |
|---|---|---|---|---|---|---|---|---|
| DEN-1 | C | G | C | A | A | A | A | C |
| 16007 | Ala | Glu | Asn | Tyr | Met | Gln | Lys | Ser |
| LAV1/ | T | A | C | T | G | G | A | T |
| PDK13 | Ala | Lys | Asn | Tyr | Val | Gln | Lys | Ser |
| VDV1 | T | A | **A** | T | G | G | **G** | T |
| Master | Ala | Lys | **Lys** | Tyr | Val | Gln | **Arg** | Ser |
| VDV1 | T | A | **A** | T | G | G | **G** | T |
| Bulk | Ala | Lys | **Lys** | Tyr | Val | Gln | **Arg** | Ser |

Complete VDV1 master seed sequence was aligned with the bulk sequence. No difference between the two sequences was observed, indicating genetic stability across passages. VDV1 shows a remarkable genetic stability with regard to its LAV1 parent.

Example 3

Characterization

The objective of these studies was to assess whether changes in attenuation markers occurred through passages.

Figure 1:
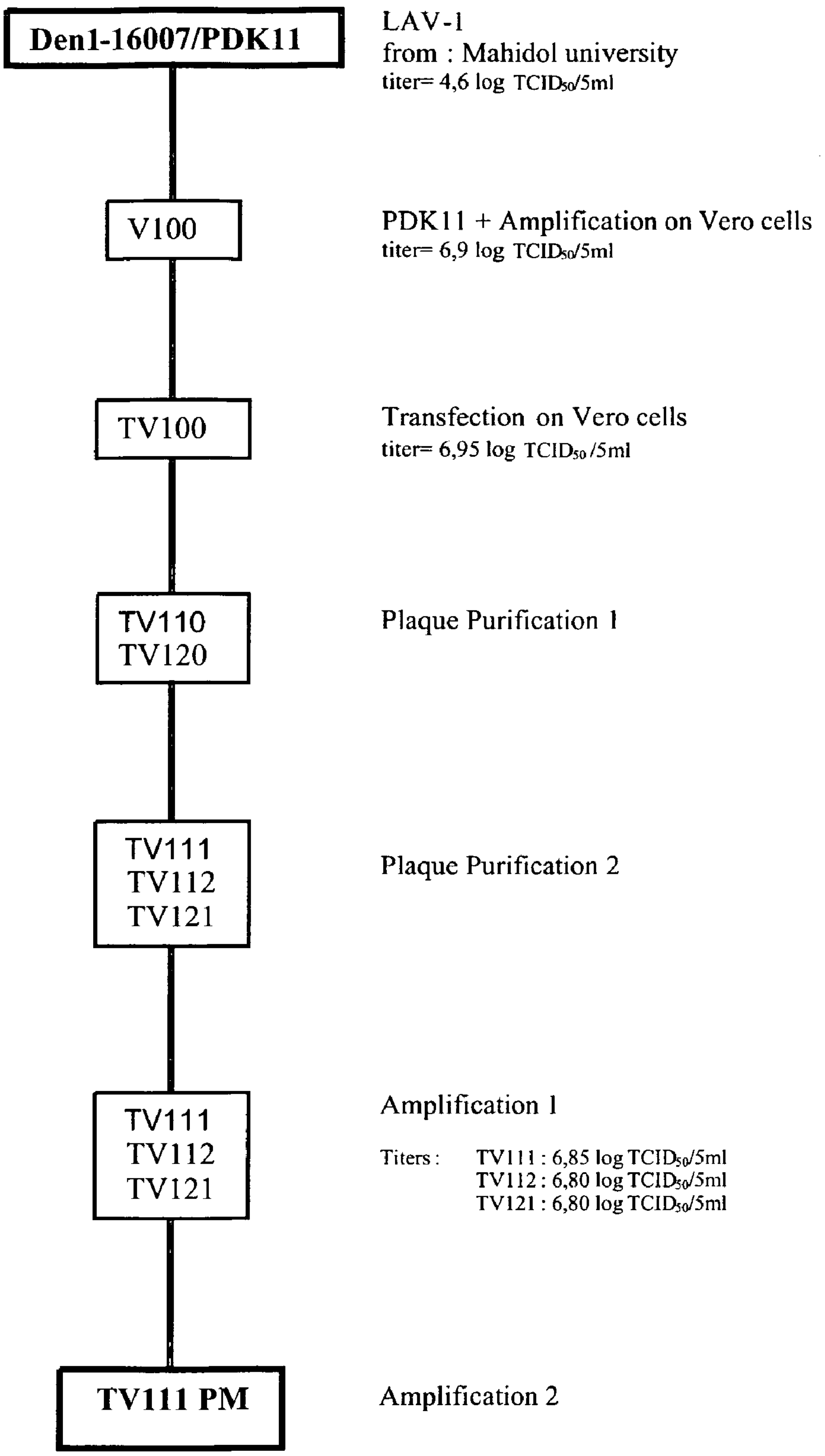
FIG. 1 is a summary of History of VDV1 pre-master seed.
Figure 2:
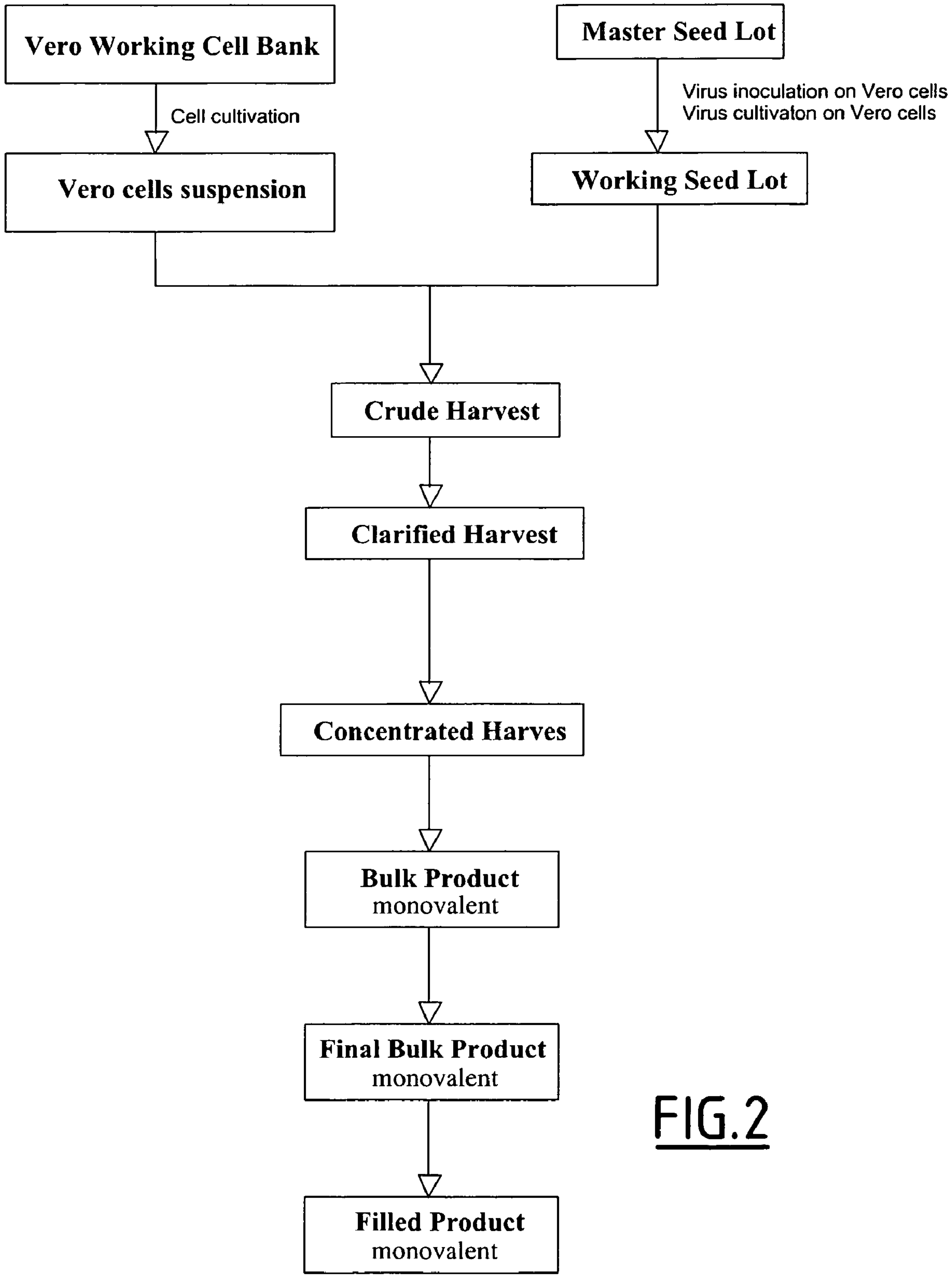
FIG. 2 is a flow chart that summarises the developed manufacturing process that gives rise to the Filled Product (monovalent), "ready to use" doses.

The flow chart shown on FIG. 2 summarises the developed manufacturing process that gives rise to the Filled Product (monovalent), "ready to use" doses Briefly, after 2 successive passages on Vero cells of the Viral Pre-Master Seeds delivered by the Research department, the respective working seeds were obtained. The final virus cultivations were also conducted by infection of a Vero cell suspension. The viruses produced are then harvested. DesoxyRiboNucleic Acid (DNA) was digested according to an enzymatic treatment. Impurities were removed by ultrafiltration. Infectious titers were enhanced by a concentration step. An aqueous buffered solution comprising cryoprotective agents (pH=7.5) is added and this 0.22-μm filtrated mixture is then diluted at the targeted dose within the same solution. The active substance is then filled into glass vials, freeze-dried, and stored before use.

3.1 Phenotypic Markers

The results are shown in Table 8. The validated tests performed for the master seed and the bulk are:

Plaque size: the assay was performed in Vero cells at 37° C. after 7 days of incubation. Sizing of the plaques was performed by Saisam v.5.2.0 (Microvision Instruments) dedicated software, after image capture with a video camera. Two populations (0.3 mm and 0.8 mm) were detected in LAV1. The major population was the smallest. After adaptation to Vero cells and biological cloning, VDV1 plaque size distribution appears homogenous, with more than 98% of the population showing a single peak, centered to 0.8 mm in diameter. These plaques are clearly distinct from plaques obtained with DEN-1 16007 virus (see FIGS. 4 and 5).

Temperature sensitivity: monovalent 1 exhibits clear restricted growth at 39° C. with respect to the non-temperature sensitive (Ts), wild-type (WT) D1-16007. This was demonstrated both by infectious titer assay and by viral RNA quantification. Master, bulk and passage 18 (10 passages after the bulk passage) of the monovalent 1 seed display 90% or more of titer reduction at 39° C., compared to 37° C.

3.2 Genotypic Markers

VDV1 vaccine strain can be distinguished from parental strains at the genomic level. Attenuation-specific loci have been identified. These loci are conserved in master and bulk seeds.

Example 4

Immunogenicity, Viremia, and Toxicology in Monkeys

The most solid and numerous data that can be obtained in monkeys concern immunogenicity and viremia. Viremia, in particular, has been identified as one of the factors associated with virulence and disease severity in humans, and then constitutes an important parameter to consider. Obviously, immunogenicity is a key parameter when testing vaccines.

Inventors have established minimal/maximal values for viremia and immunogenicity.

TABLE 9

Minimal requirements for responses induced by Dengue vaccine candidates in monkeys, as measured in Vero or LLC-MK2 cells by plaque assay (these cells being considered equivalent in such an assay)

| Viremia mean duration (days) (all serotypes being considered) | Viremia mean peak titer (log 10 pfu) (all serotypes being considered) | Mean neutralizing titer Day 30 (for each serotype) PRNT 50 |
|---|---|---|
| ≦3 days | ≦1.5-2 | ≧80 |

pfu: plaque forming unit
PRNT 50: Plaque Reduction Neutralization Titer 50 (titre corresponding to a reduction of 50% of plaque number)

4.1 Material and Methods 4.1.1 Monkey Experiments

Monkey experiments were carried out according to European guidelines regarding animal experiments.

Immunizations were performed on cynomolgus monkeys (*Macaca fascicularis*) originating from Mauritius (CRP Le Vallon). Monkeys were quarantined for 6 weeks in the animal facility of Sanofi Pasteur before immunization.

TABLE 8

Summary of DEN-1 viral phenotypes

| | Temperature sensitivity (Percent titer reduction at 39° C.)$_{Fold\text{-}reduction}$ | | | | | Neurovirulence in newborn Swiss Webster mice | |
|---|---|---|---|---|---|---|---|
| Virus | Score | Day 3 | Day 4 | Day 5 | Day 6 | Mortality$_n$* | AST (S.D.) |
| D1-16007 | − | $62.1_{2.6}$ | $59.3_{2.5}$ | $56.3_{2.3}$ | $(-28.5_{-1.4})$ | $6.25\%_{16}$ | 19.0(0.0) |
| D1-PDK13 | + | $87.1_{7.8}$ | $91.3_{11.5}$ | $95.5_{22.2}$ | $96.5_{28.6}$ | $0.00\%_{16}$ | n.a. |
| VDV1 MS | + | $97.2_{35.7}$ | $97.7_{43.5}$ | $98.8_{83.3}$ | $99.5_{200.0}$ | $0.00\%_{16}$ | n.a. |

*n: number of animals

Monkeys were immunized by subcutaneous (SC) route in the arm with vaccines in a volume of 0.5 ml (see each respective section). After light anesthesia with ketamine (Imalgene, Merial), blood was collected by puncture of the inguinal or saphene veins. At days 0 and 28, 5 ml of blood were sampled for evaluating antibody responses while between days 2 and 10 only 1 ml of blood was sampled for evaluating viremia. Blood was collected on ice and kept on ice until serum separation. To do so, blood was centrifuged for 20 minutes at 4° C., and serum collected and stored at −80° C. until testing in Rich Kinney's laboratory. Shipment to USA was performed in dry ice.

4.1.2 Viremia and Neutralizing Antibody Responses (Plaque Reduction Neutralization Test, PRNT)

All analyses were performed in the laboratory of R. Kinney in CDC, Fort Collins, USA. Serum samples were shipped and stored at −80° C. until the time of testing. At the time of first thawing, the samples were tested for viremia, and a 1:5 dilution of the serum was made. The 1:5 serum dilutions were inactivated for 30 min at 56° C. before testing for neutralizing antibodies.

4.1.2.1 Viremia 0.125 ml of serum was added to 0.125 ml of diluent (RPMI medium) in the first well of 96-well plate and serial 10-fold dilution series were done, transferring 0.025 ml into 0.225 ml of diluent for each dilution. 0.2 ml of $10^{0.3}$-$10^{5.3}$ dilution series was plated in 6-well plate of Vero cells (virus was adsorbed at 37° C. for 1.5 hour, overlayed with 4 ml of agarose lacking neutral red, overlayed 6-7 days later with 2 ml of agarose containing neutral red, and plaques counted). The limit of virus detection was =10 PFU/ml. For controls stock DEN-1 6007 PDK-13 (LAV1) vaccine was plated.

4.1.2.2 PRNT (Plaque Reduction Neutralization Test)

Neutralizing antibodies were quantified as described in Huang et al. (2000). Briefly, 0.2 ml of heat-inactivated, 1:5 dilution of serum was added to the first well of 96-well plate and serial 2-fold dilution series were made, transferring 0.1 ml into 0.1 ml of diluent (RPMI medium) for each dilution. This resulted in a 1:10-1:320 serum dilution series. 0.1 ml of DEN virus (60-160 PFU; parental DEN1 16007 virus) was added to each serum dilution well for a total of 0.2 ml of serum-virus mixture. 96-well plates were incubated overnight at 4° C. 0.1 ml of serum-virus mixtures (containing 30-80 PFU of input virus) were plated in 6-well Vero plates (as indicated above in the Viremia section) and plaques were counted after staining with neutral red. Multiple back titrations of the input viruses at 2-fold, 1-fold, and 0.5-fold test concentrations provided direct experimental determination of the input PFU, which was the basis for determining 50% ($PRNT_{50}$) and 70% ($PRNT_{70}$) endpoint antibody titers. A negative serum result should have a neutralizing antibody titer of <1:10. Sera showing neutralization titers of 320 were retested at dilutions 1:80-1:2560 for determination of endpoint titer.

4.2 Evaluation of VDV Candidates 4.2.1 VDV 1/Pre-master

Purification/selection of D1 candidate has been conducted as described in example 1. The selected clones (based on phenotypic markers and sequence) have been tested in sanofi pasteur as described in Material and Methods (Marcy l'Etoile animal facility, I15) on male cynomolgus macaques (*Macaca fascicularis*, mean weight 3.1 kg) originating from CRP Le Vallon, Mauritius.

After immunization on D0, viremia was followed from D2 to D10, and immunogenicity measured at D0 and D28. All viruses and vaccines, when in liquid form, were kept at −70° C.

LAV1: titre: $10^{3.9}$ $DICC_{50}$/ml; lyophilized, resuspended in 0.5 ml of PBS (containing $Ca^{2+}$ and $Mg^{2+}$; $CaCl_2.2H_2O$ 0.133 g/l; $MgCl_2.6H_2O$, 0.1 g/l) and administered in totality.

Premaster VDV1 DEN1-TV111: Titre: $10^{5.9}$ $DICC_{50}$/ml; liquid, diluted at $10^{5.3}$ pfu/ml in PBS (containing $Ca^{2+}$ and $Mg^{2+}$; $CaCl_2.2H_2O$ 0,133 g/l; $MgCl_2.6H_20$, 0.1 g/l); 0.5 ml administered.

Injection was done by SC route in the arm with a 23G1 needle, at a $10^5$ $DICC_{50}$ dose for VDV1.

The results are as presented in Table 10. Titrations at day 28 were carried out in triplicate ($PRNT_{70}$) or in duplicate ($PRNT_{50}$).

TABLE 10

VDV1 PreMaster immunogenicity
AvP monovalent VDV1 (Exp A) DEN Monkey study (F. Mi.DEN003.Si): PRNT and Viremia Results

| | | Neutralizing Antibody Titer | | | | Viremia (PFU/ml in Vero cells) | | | | | | | | | |
|---|---|---|---|---|---|---|---|---|---|---|---|---|---|---|---|
| | | Day (−15) | | Day 28 | | Day | Day | Day | | | | | | | Day |
| Serum | Group | $PRNT_{70}$ | $PRNT_{50}$ | $PRNT_{70}$ | $PRNT_{50}$ | −15 | 2 | 3 | Day 4 | Day 5 | Day 6 | Day 7 | Day 8 | Day 9 | 10 |
| AD 333 | LAV DEN-1 | <10/<10 | <10 | 320/160/160 | 160/320 | 0 | 0 | 0 | 0 | 0 | 0 | 0 | 0 | 0 | 0 |
| AC 763 | | <10/<10 | <10 | 640/640/640 | 1280/1280 | 0 | 0 | 0 | 0 | 0 | 0 | 0 | 0 | 50 | 150 |
| AD 209 | | <10/<10 | <10 | 320/160/160 | 160/320 | 0 | 0 | 0 | 0 | 0 | 0 | 0 | 0 | 0 | 0 |
| AC 755 | | <10/<10 | <10 | 160/80/160 | 160/160 | 0 | 0 | 0 | 0 | 0 | 0 | 50 | 0 | 0 | 0 |
| AC 775 | VDV DEN-1 | <10/<10 | <10 | 160/80/80 | 160/160 | 0 | 0 | 0 | 0 | 0 | 0 | 0 | 0 | 0 | 0 |
| AC 881 | TV111 | <10/<10 | <10 | 20/10/10 | 20/20 | 0 | 0 | 0 | 0 | 0 | 0 | 0 | 0 | 0 | 0 |
| AD 145 | | <10/<10 | <10 | 320/80/80 | 160/80 | 0 | 0 | 0 | 0 | 0 | 0 | 0 | 0 | 0 | 0 |
| AD 113 | | <10/<10 | <10 | 20/10/10 | 20/20 | 0 | 0 | 0 | 0 | 0 | 0 | 0 | 0 | 0 | 0 |
| Virus DEN-1 | Exp#1 112PFU | Exp#2 45PFU | Exp#3 101PFU | | | | | | | | | | | | |

Briefly, responses were rather homogeneous within each group, and some clear tendencies could be identified for each construct. No dramatic differences were found between VDV1 and LAV1: low and late viremia was observed in some LAV1 monkeys. VDV1 looked satisfactory, and in particular presented no viremia.

4.2.2 VDV 1 Bulk

As immunogenicity of the vaccines had been tested at the Premaster stage, a further experiment was designed to test each monovalent at the Bulk stage.

Male *Macaca fascicularis* monkeys were used as before, originating from C.R.P. Le Vallon, Ile Maurice (24 monkeys, mean weight 3.4 kg).

VDV1; Batch: Titre: 8.37 log 10 $DICC_{50}$/ml

Placebo: PBS with $Ca^{2+}$ and $Mg^{2+}$

Vaccines were diluted at $10^{5.3}$ $DICC_{50}$/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered by SC route in the arm with a 23G1 needle, corresponding to a dose of $10^5$ $DICC_{50}$.

Viremia and immunogenicity have been measured as usual in CDC by R Kinney. The results are shown in Table 11.

VDV1 monovalent vaccine induced a significant immune response while viremia was absent. Thus, this monovalent VDV1 fulfilled the success criteria initially defined in monkeys.

No histopathological signs of pathogenicity were observed in the monkey brains injected with VDV1 seeds.

Example 5

Safety of Monovalent VDV1 in Healthy, Flavivirus-Naive Adults Aged 18 to 40 Years The aim of this phase 1 trial is to document the safety, viremia, and immunogenicity profiles of monovalent VDV1 at a virus concentration of $10^4$ $CCID_{50}$ compared to Stamaril® (used as control group) in flavivirus-naive adults. Single injections are given, with follow-up at 6 and 12 months. For safety precaution, sequential inclusions are performed in the study.

Enrollment and vaccinations are therefore staggered; a 1st cohort (n=4 per group, total n=12) have been vaccinated. The safety data collected up to Day 28 have been reviewed by an Independent Data Monitoring Committee (IDMC) and by the Royal Adelaide Hospital Investigational Drugs Subcommittee (IDSC) before deciding to proceed with the vaccination of the remaining subjects (n=8 per group, total n=16). A schematic representation of the trial design is provided in FIG. 6.

TABLE 11

VDV Bulk VDV1 immunogenicity and viremia
Monkey study (F.MI.DEN004.Mk): Monovalent and Tetravalent VDV1

| | | Neutralizing Antibody Titer | | | | Viremia (PFU/ml in Vero cells) | | | | | | | | |
|---|---|---|---|---|---|---|---|---|---|---|---|---|---|---|
| | | Day (−14) | | Day 28 | | Day | Day | Day | Day | | Day | | Day | |
| Monkey | Group | $PRNT_{50}$ | $PRNT_{70}$ | $PRNT_{50}$ | $PRNT_{50}$ | −14 | 2 | 3 | 4 | Day 5 | 6 | Day 7 | 8 | Day 9 |
| AE 484 | VDV DEN-1 | — | — | 14 | 5 | 0 | 0 | 0 | 0 | 0 | 0 | 0 | 0 | 0 |
| AE 627 | | — | — | 8122 | 4558 | 0 | 0 | 0 | 0 | 5 | 0 | 0 | 0 | 0 |
| AF 115 | | — | — | 359 | 202 | 0 | 0 | 0 | 0 | 0 | 0 | 0 | 0 | 0 |
| AF 227 | | — | — | 557 | 367 | 0 | 5 | 0 | 5 | 0 | 0 | 0 | 0 | 0 |
| Geo Mean | Homologous response | — | — | 388 | 203 | | | | | | | | | |
| AE 538 | Placebo | —/—/—/— | —/—/—/— | 2.5/—/2/2 | —/—/—/— | 0 | 0 | 0 | 0 | 0 | 0 | 0 | 0 | 0 |
| AE 548 | | —/—/—/— | —/—/—/— | —/—/1/2 | —/—/—/— | 0 | 0 | 0 | 0 | 0 | 0 | 0 | 0 | 0 |
| AE 556 | | —/—/1.5/2 | —/—/—/— | 1/—/—/— | —/—/—/— | 0 | 0 | 0 | 0 | 0 | 0 | 0 | 0 | 0 |
| AE 572 | | —/—/1.5/5 | —/—/1.5/2 | 5/—/—/2 | —/—/—/— | 0 | 0 | 0 | 0 | 0 | 0 | 0 | 0 | 0 |
| Geo Mean | Response against the four serotypes | —/—/1.2/3 | —/—/1/1 | 2/—/ 1.2/1.6 | —/—/—/— | | | | | | | | | |
| | | D1/D2/ D3/D4 | D1/D2/ D3/D4 | D1/D2/ D3/D4 | D1/D2/ D3/D4 | | | | | | | | | |

4.3 Neurovirulence Tests in Monkeys

For each virus type, 10 cynomolgus monkeys from Mauritius were inoculated with VDV1 master seed by the intracerebral route ($10^{7.23}$ $CCID_{50}$/mL in the thalamus of each hemisphere). At the end of the test, the monkeys were sacrificed and perfused with formalin solution. Tissue samples were taken from the brain of each monkey (medulla oblongata, pons and cerebellum, midbrain, thalamus including the left and the right parts, the left and the right of the cerebral cortex). Sections were cut at a thickness of 8 μm and stained by eosin and gallocyanin.

After administration of the vaccine the patient are regularly submitted to various clinical examination and testing. A summary of this follow up is given in table 12 below.

The enrolled population consists of adults aged 18 to 40 years (i.e. the day of the 18th birthday to the day before the 41st birthday) on day of inclusion who are flaviviruses-naïve [persons presenting vaccination against flavivirus diseases (e.g. yellow fever, Japanese encephalitis, dengue fever); or history of flavivirus infection (confirmed either clinically, serologically or microbiologically) or previous residence in or travel to areas with high dengue infection endemicity (whatever the duration), or residence in or travel to North Queensland for 2 weeks or more) were excluded]

TABLE 12

Flow chart for follow up

| | Visit Number | | | | | | | | | | | |
|---|---|---|---|---|---|---|---|---|---|---|---|---|
| | V01 | V02 | V03 | V04 | V05 | V06 | V07 | V08 | V09 | V10 | V11 | V12 |
| | Trial timelines ¤ | | | | | | | | | | | |
| | D 0 | D 2 | D 4 | D 6 | D 8 | D 10 | D 12 | D 14 | D 16 | D 28 | D 180 | D 365 |
| | Time Windows | | | | | | | | | | | |
| | | | | | | ±1 d | ±1 d | | | ±4 d | ±15 d | ±30 d |
| Clinical Examination | √ | √ | √ | √ | √ | √ | √ | √ | √ | √ | √ | √ |
| Vital signs (BP, pulse rate) | √ | | | | | | | | | | | |
| Oral temperature | √ | √ | √ | √ | √ | √ | √ | √ | √ | √ | | |
| Blood Sampling: | | | | | | | | | | | | |
| Serology HBV/HCV/HIV | √ | | √ | | √ | | √ | | √ | √ | | |
| Biological Safety | √ | √ | √ | √ | √ | √ | √ | √ | √ | | | |
| Viremia | √ | | | | | | | | √ | √ | √ | √ |
| Immunogenicity | √ | √ | √ | √ | √ | √ | √ | √ | √ | √ | | |
| Cytokines in serum | √ | | | | | | | | | √ | | |
| PBMCs for T cell (subset) | √ | | | | | | | | | √ | | |
| immediate surveillance | √ | | | | | | | | | | | |
| Local & systemic events | √ | √ | √ | √ | √ | √ | √ | √ | √ | √ | √ | √ |

V: Visit
D: day
¤Time intervals between visits will be calculated from the date of study vaccination which might differ from the date of visit (e.g. in case a temporary exclusion criterion is met). V06 and V07 must be done with at least 1-day interval.

The products tested are:

The vaccine evaluated is a lyophilised product in a vial that is reconstituted extemporaneously with the diluent provided separately:

Active ingredient: 4±0.5 $\log_{10}$ $CCID_{50}$ of either monovalent Vero dengue virus serotype 1 (VDV1) per 0.5 mL dose;

Diluent: Sterile NaCl 4% solution for vaccine reconstitution.

The reconstituted vaccine, i.e 0.5 mL of NaCl 4% solution of monovalent VDV1, should be used immediately or be maintained until use +2° C. and +8° C.

The 0.5 mL vaccine dose is administered subcutaneously in the deltoid region.

The control vaccine Stamaril®, is a yellow fever vaccine produced by Aventis Pasteur. Stamaril® is presented as a lyophilised, avian-leukosis-free, stabilised product to be reconstituted with a diluent immediately before use. (Active ingredient: Live attenuated yellow fever virus (17D strain): ≧1,000 mouse Lethal Dose 50% ($LD_{50}$)/Diluent: Sterile NaCl 4% solution).

The control vaccine is administered subcutaneously in the deltoid region.

The preliminary results of the trial are reported in Table 13 below.

TABLE 13 preliminary safety data

| | Day 0 | Day 1 | Day 2 | Day 3 | Day 4 | Day 5 | Day 6 | Day 7 | Day 8 | Day 9 | Day 10 | Day 11 | Day 12 | Day 13 |
|---|---|---|---|---|---|---|---|---|---|---|---|---|---|---|
| LOCAL SOLICITED | | | | | | | | | | | | | | |
| Pain | 1 | | | | | | | | | | | | | |
| Erythema | | | | | | | | | | | | | | |
| Induration | | | | | | | | | 1 | | | | | |
| Edema | | | | | | | | | | | | | | |
| LOCAL UNSOLICITED | | | | | | | | | | | | | | |
| Bruise | | 1 | 1 | | | | | | | | | | | |
| Pruritis | | | | | | | | | | | | | | |
| OTHER SOLICITED | | | | | | | | | | | | | | |
| Temp ≧37.5 C. | | | 1 | | | 1 | | | | | | | | |
| Rigors | | | 1 | 1 | | | | | 1 | | | | | |
| Malaise | | 2 | 1 | 1 | 1 | 1 | 1 | 1 | 1 | | | 2 | 1 | 2 |
| Asthenia | | 1 | 2 | 1 | 1 | 2 | 1 | | 1 | | | 2 | 1 | 1 |
| Anorexia | | | 1 | 1 | 1 | | | | | | | 1 | 1 | 1 |

TABLE 13-continued preliminary safety data

| | Day 0 | Day 1 | Day 2 | Day 3 | Day 4 | Day 5 | Day 6 | Day 7 | Day 8 | Day 9 | Day 10 | Day 11 | Day 12 | Day 13 |
|---|---|---|---|---|---|---|---|---|---|---|---|---|---|---|
| Nausea | | 1 | 2 | 1 | | 1 | 1 | | 1 | | | 1 | 1 | 2 |
| Vomiting | | | 1 | 1 | | 1 | 1 | | | | | 1 | 1 | |
| Stomach Pain | 1 | 1 | 2 | 2 | 1 | 1 | 1 | | 1 | | | 1 | 1 | 1 |
| Headache | 2 | 1 | 2 | 2 | | 1 | 1 | 1 | 2 | 1 | | 1 | 1 | 1 |
| Myalgia | | | 1 | 1 | | 1 | | | | | | 1 | 1 | 2 |
| Arthralgia | | | 1 | 1 | | 1 | 1 | | | | | 1 | 1 | 1 |
| Avoidance of light | | | | | | | 1 | 1 | | | | 1 | | |
| Conjunctivitis | | | | | | | | | | | | | | |
| Eye Pain | | | | | | | 1 | 1 | | | | | | |
| RASH | | | | | | | | | | | | | | |
| Macular | | | | | | | | | | 1 (1%) | | | | |
| Papular | | 1 (1%) | | | | | | | | | | | | |
| Maculo-papular | | | | | | | | | | | | | 1 (90%) | 1 (90%) |
| OTHER UNSOLICITED | | | | | | | | | | | | | | |
| Decreased WCC | | | | | | | | | 2 | | 1 | | | |
| Neutropenia | | | | | | | | | 2 | | 1 | | | |
| Increased aPPT | | | | | 1 | | | | 1 | | | | | |
| Elevated CK | | | | | | | | | 1 | | | | | |
| Odd dreams | | | | | | | 1 | | | | | | | |
| Low abdo pain (kidneys/liver) | | | | | | | | | | | | 1 | 1 | 1 |
| Diarrhoea | | 1 | 1 | 1 | 1 | 1 | | | | | 1 | 1 | 1 | 1 |
| Sore throat | | | | 1 | | | | | | | | | | 1 |
| Cough | | | | | | | | | | | | | | 1 |
| Early menstruation | | | | | | | | | 1 | | | | | |
| Tiredness | | | | | | | | | | | 1 | | | |

Table 13 shows that biological abnormalities (WCC reductions, platelet count reductions) have all been mild. The symptoms have been mainly malaise, nausea, diarrhea and occasional vomiting. They have been of moderate severity. One significant rash—typical "viral" maculopapular rash, onset day 12, 90% coverage.

The safety data of the second cohort are also satisfactory with no biological abnormality recorded. All subjects have antibody response 28 days after vaccination against dengue 1 (titer between 1315 and 13150).

REFERENCES

Bhamarapravati, N and Yoksan S. (1997). Dengue and Dengue Hemorrhagic Fever.Live attenuated tetravalent dengue vaccines, CABI Publishing, 367-379.

DeFraites R F, Smoak B L, Trofa A F, Hoke C H, Kanesathasan N, King A, MacArthy P O, et al. Dengue fever among U.S. military personnel—Haiti, September-November, 1994. MMWR 1994; 43: 845-848.

Dunnen and Antonarakis (2000) Mutation nomenclature extensions and suggestions to describe complex mutations: a discussion. Hum Mutation. 15:7-12; Erratum in: Hum Mutat 2002; 20(5):403

Gubler D J. Dengue. (1988) In: Epidemiology of arthropod-borne viral disease. Monath T P M, editor, Boca Raton (Fla.): CRC Press: 223-60

Gubler D J, Kuno G. Dengue and Dengue Hemorrhagic Fever. CAB International Publishing 1997

Gubler D. Epidemic dengue/dengue hemorrhagic fever as a public health, social and economic problem in the 21st century. (2002) TRENDS in Microbiology. 10:100-103

Huang et al. (2000). J. Virol 74; 3020-3028.

Kautner I, Robinson M J, Kubnle U. (1997) Dengue Virus infection: Epidemiology, pathogenesis, clinical presentation, diagnosis, and prevention. J of Pediatrics; 131:516-524

Monath, T P. (1994) Dengue: the risk to developed and developing countries. Proc Natl Acad Sci; 91: 2395-2400.

Rigau-Pérez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue hemorrhagic fever. Virology; 257: 1-6

Sabin A B. (1952) Research on dengue during World War II. Am J Trop Med Hyg; 1: 30-50

Shirtcliffe P, Cameron E, Nicholson K G, Wiselka M J. (1998) Don't forget dengue! Clinical features of dengue fever in returning travelers. J Roy Coll Phys Lond.; 32: 235-237.

Thompson J D, Higgins D G, and Gibson T J. (1994) CLUSTAL W: improving the sensitivity of progressive multiple sequence alignment through sequence weighting, position-specific gap penalties and weight matrix choice. Nucl. Acids. Res., 22 (22), 4673-4680

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30.

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J lnf Dis; 181: 2-9.

WHO Technical Guide, 1986. Dengue haemorrhagic fever: diagnosis, treatment and control, p1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

The invention claimed is:

1. A live attenuated dengue-1 virus strain which comprises sequence SEQ ID NO: 3 wherein at least nucleotides at positions 5962 and 7947 are mutated, with the proviso that the following nucleotides are not mutated: 1323, 1541, 1543, 1545, 1567, 1608, 2363, 2695, 2782, 5063, 6048, 6806, 7330, and 9445.

2. The dengue-1 virus strain according to claim 1, wherein the nucleotide at position 2719 is further mutated.

3. The dengue-1 virus strain according to claim 1, wherein SEQ ID NO: 3 comprises the mutations 2719 G>A, 5962 C>A, and 7947 A>G.

4. The dengue-1 virus strain according to claim 1, which further comprise a substitution of one or more nucleotides in a given codon position which results in no alteration in the amino acid encoded at that position.

5. The dengue-1 virus strain according to claim 1, which comprises SEQ ID NO: 1.

6. An immunogenic composition comprising a live attenuated dengue-1 virus strain which comprises sequence SEQ ID NO: 3 wherein at least nucleotides at positions 5962 and 7947 are mutated, with the proviso that the following nucleotides are not mutated: 1323, 1541, 1543, 1545, 1567, 1608, 2363, 2695, 2782, 5063, 6048, 6806, 7330, and 9445, in a pharmaceutically acceptable carrier.

7. The immunogenic composition according to claim 6, wherein said live attenuated dengue-1 virus strain comprises SEQ ID NO: 3 in which A at position 2719 is substituted for G, A at position 5962 is substituted for C, and G at position 7947 is substituted for A.

8. The immunogenic composition according to claim 6, wherein said live attenuated dengue-1 virus strain further comprises a substitution of one or more nucleotides in a given codon position which results in no alteration in the amino acid encoded at that position.

9. The immunogenic composition according to claim 6, wherein said live attenuated dengue-1 virus strain comprises SEQ ID NO: 1.

10. The immunogenic composition according to claim 6, which further comprises at least one live attenuated dengue virus selected from the group consisting of serotype 2, serotype 3, and serotype 4.

* * * * *

UNITED STATES PATENT AND TRADEMARK OFFICE

CERTIFICATE OF CORRECTION

PATENT NO. : 7,641,907 B2
APPLICATION NO. : 11/449876
DATED : January 5, 2010
INVENTOR(S) : Kinney et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 206 days.

Signed and Sealed this

Sixteenth Day of November, 2010

David J. Kappos

*Director of the United States Patent and Trademark Office*